(12) United States Patent
Hicks et al.

(10) Patent No.: US 12,304,899 B2
(45) Date of Patent: May 20, 2025

(54) FACTOR XI ACTIVATION INHIBITORS

(71) Applicant: Merck Sharp & Dohme LLC, Rahway, NJ (US)

(72) Inventors: Jacqueline D. Hicks, Watchung, NJ (US); John S. Debenham, Scotch Plains, NJ (US); Amjad Ali, Freehold, NJ (US); Lan Wei, Berkeley Heights, NJ (US); Tianying Jian, Westfield, NJ (US); Dexi Yang, Livingston, NJ (US); Anthony K. Ogawa, San Mateo, CA (US); Wenlang Fu, Madison, NJ (US); Matthew Lombardo, Flemington, NJ (US); Rongze Kuang, Green Brook, NJ (US); Meng Yang, Westfield, NJ (US); Sung-Sau So, Verona, NJ (US); Kenneth Ellsworth, Cranbury, NJ (US); Peter Nizner, Fanwood, NJ (US); Daniel A. Tatosian, Berkeley Heights, NJ (US); Robert R. Wilkening, Maplewood, NJ (US); Jun Wang, Avon, CT (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 741 days.

(21) Appl. No.: 17/613,988

(22) PCT Filed: May 26, 2020

(86) PCT No.: PCT/US2020/034468
§ 371 (c)(1),
(2) Date: Nov. 24, 2021

(87) PCT Pub. No.: WO2020/243049
PCT Pub. Date: Dec. 3, 2020

(65) Prior Publication Data
US 2022/0235033 A1    Jul. 28, 2022

Related U.S. Application Data

(60) Provisional application No. 62/854,749, filed on May 30, 2019.

(51) Int. Cl.
*C07D 401/14* (2006.01)
*C07D 405/14* (2006.01)
*C07D 413/14* (2006.01)
*C07D 417/14* (2006.01)
*C07D 471/04* (2006.01)
*C07D 471/14* (2006.01)

(52) U.S. Cl.
CPC ......... *C07D 401/14* (2013.01); *C07D 405/14* (2013.01); *C07D 413/14* (2013.01); *C07D 417/14* (2013.01); *C07D 471/04* (2013.01)

(58) Field of Classification Search
CPC .. C07D 401/14; C07D 405/14; C07D 413/14; C07D 417/14; C07D 471/04
See application file for complete search history.

(56) References Cited

U.S. PATENT DOCUMENTS

2008/0045568 A1  2/2008  Deng et al.
2008/0300239 A1  12/2008  Adams et al.
2014/0309227 A1  10/2014  Bungard et al.

FOREIGN PATENT DOCUMENTS

WO  2013056034 A1  4/2013
WO  2018093695 A1  5/2018

OTHER PUBLICATIONS

Al-Horani et al., Factor XIa inhibotrs: A review of the patent literature, Expert Opinion on Therapeutic Patents, 2016, 323-345, vol. 26 No. 3.
Colman, Robert W., Contact Activation Pathway: Inflammatory, Fibrinolytic, Anticoagulant, Antiadhesive, and Antiangiogenic Activities, Hemostasis and Thrombosis, 2001, 103-121, Chapter 6.
Gao, Qinghe et al., Coproduct Promoted Povarov Reaction: Synthesis of Substituted Quinolines from Methyl Ketones, Arylamines, and α-Ketoesters, The Journal of Organic Chemistry, 2015, 5984-5991, 80.
International Search Report and Written Opinion for PCT/US2020/034468, mailed Sep. 10, 2020; 7 pages.
Kleinschnitz, Christoph et al., Targeting coagulation factor XII provides protection from pathological thrombosis in cerebral ischemia without interfering with hemostasis, JEM, 2006, 513-518, 203.

(Continued)

*Primary Examiner* — Shawquia Jackson
(74) *Attorney, Agent, or Firm* — Daniel Woods; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XI activation inhibitors.

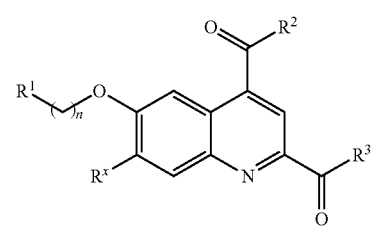

13 Claims, No Drawings

(56) References Cited

OTHER PUBLICATIONS

Pubmed Compound Record for CID 69352821, '[6-[2-(1-Methylpyrrol-2-yl)ethoxy]quinolin-2-yl]-pyrrolidin-1-ylmethanone', U.S. National Library of Medicine, Dec. 1, 2012 (Dec. 2012), pp. 1-8: p. 2 (https://pubchem.ncbi.nlm.nih.gov/substance/69352821).
Renné, Thomas et al., Defective thrombus formation in mice lacking coagulation factor XII, JEM, 2005, 271-281, 202.
Schmaier, Alvin H., Contact Activation, Thrombosis and Hemorrhage, 1998, 105-127, Chapter 5.
Shariat-Madar, Zia et al., Bradykinin B2 receptor knockout mice are protected from thrombosis by increased nitric oxide and prostacyclin, Blood, 2006, 192-199, 108.

FACTOR XI ACTIVATION INHIBITORS

CROSS-REFERENCE TO RELATED APPLICATIONS

This application is the 371 national phase application of International Patent Application No. PCT/US2020/034468, filed May 26, 2020, which claims priority to U.S. Provisional Patent Application No. 62/854,749, filed May 30, 2019, hereby incorporated by reference in their entirety.

BACKGROUND OF THE INVENTION

Factor XI undergoes proteolysis to afford its activated form, factor XIa, which functions as a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XI to generate factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

SUMMARY OF THE INVENTION

The present invention relates to compounds of Formula I:

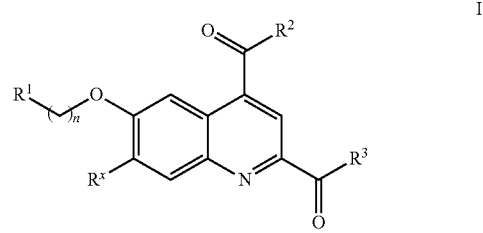

and pharmaceutically acceptable salts thereof. The compounds of Formula I are selective Factor XI activation inhibitors, and as such may be useful in the treatment, inhibition or amelioration of one or more disease states that could benefit from inhibition of Factor XI, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I.

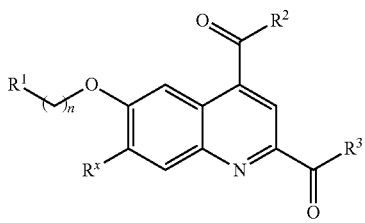

wherein
$R^1$ is phenyl or heteroaryl, which may be monocyclic or bicyclic, wherein said phenyl and heteroaryl groups are optionally substituted with one to three substituents independently selected from the group consisting of halo, oxo, cyano, $R^4$, $OR^4$, $R^6$ and $NO_2$;
$R^2$ is piperidinyl, $NR^4R^5$ or $NR^4R^6$, wherein said piperidinyl group is optionally substituted with one to three halo;
$R^3$ is heterocyclyl, which may be monocyclic or bicyclic, or $NHC(CH_3)_2R^6$, wherein said heterocyclyl is optionally substituted with one to three substituents independently selected from the group consisting of halo, cyano, $R^4$, $OR^4$, $R^6$, $CONR^4R^5$, $NR^4COR^5$, $(C_{1-3}$ alkyl$)R^6$ and $SO_2R^4$,
$R^4$ is hydrogen or $C_{1-6}$ alkyl, which is optionally substituted with one to three halo;
$R^5$ is hydrogen or $C_{1-6}$ alkyl, which is optionally substituted with one to three halo;
$R^6$ is phenyl, $C_{3-6}$ cycloalkyl, heterocyclyl or heteroaryl, wherein said heteroaryl is optionally substituted with one to three substituents independently selected from the group consisting of $C_{1-6}$ alkyl or halo;
$R^x$ is hydrogen, halo or $C_{1-6}$ alkyl;
n is an integer from one to three;
or a pharmaceutically acceptable salt thereof.

In an embodiment of the invention, $R^1$ is selected from benzoimidazolyl, benzoisoxazolyl, benzooxadiazolyl, benzooxazolyl, benzothiadiazolyl, benzothiazolyl, benzotriazolyl, dihydroindazolyl, dihydroisobenzofuranyl, imidazopyridinyl, phenyl, pyrazolopyridinyl, pyridinyl or pyrrolyl wherein said groups are optionally substituted with one or two substituents independently selected from the group consisting of methyl, chloro, fluoro, oxo, cyano, $NO_2$, $CF_3$, $OCHF_2$, $OCF_3$ and $OCH_3$. In a class of the invention, $R^1$ is heteroaryl, which is bicyclic, and is optionally substituted with one to three substituents independently selected from the group consisting of halo, oxo, cyano and $R^4$.

In an embodiment of the invention, $R^2$ is piperidinyl.

In an embodiment of the invention, $R^3$ is piperidinyl, piperazinyl, azaspiroocatnyl or pyrrolidinyl, wherein said groups are optionally substituted with one or two substituents independently selected from the group consisting of methyl, fluoro, hydroxyl, cyano, pyrazolyl, phenyl, triazolyl, piperidinyl, $CONH_2$, $CH_2CF_3$, $CH(CH_3)CF_3$, $CH_2CHF_2$ and $SO_2CH_3$. In a class of the invention, $R^3$ is piperidinyl, which is optionally substituted with one or two substituents independently selected from the group consisting of methyl, fluoro, hydroxyl, cyano, pyrazolyl, phenyl, triazolyl, piperidinyl, $CONH_2$, $CH_2CF_3$, $CH(CH_3)CF_3$, $CH_2CHF_2$ and $SO_2CH_3$.

In an embodiment of the invention, $R^x$ is halo. In a class of the invention, $R^x$ is fluoro.

In an embodiment of the invention, n is one. In another embodiment of the invention, n is two. In another embodiment of the invention, n is three.

Reference to the preferred classes and subclasses set forth above is meant to include all combinations of particular and preferred groups unless stated otherwise.

Specific embodiments of the present invention include, but are not limited to the compounds identified herein as Examples 1 to 76, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes methods for treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, comprising administering a composition of the compound of the invention to a mammal in need thereof.

The invention also includes a method for reducing the thrombogenicity of a surface in a mammal by attaching to the surface, either covalently or noncovalently, a compound of the invention.

The invention also includes a compound of the invention, or a pharmaceutically acceptable salt thereof, for use in the manufacture of a medicament for inhibiting thrombin, inhibiting thrombus formation, treating thrombus formation or preventing thrombus formation in a mammal. In addition, the invention includes a compound of the invention, or a pharmaceutically acceptable salt thereof, for use in therapy.

Compounds of the invention are Factor XI activation inhibitors and may have therapeutic value in, for example, preventing coronary artery disease. The compounds of the invention have improved pharmacokinetic profiles compared to compounds known in the art.

Furthermore, some of the compounds of the invention have a better combination of potency, efficacy and pharmacokinetic properties compared to known compounds.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enantiomer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$).

Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "preventing," or "prohylaxis," as used herein, refers to reducing the likelihood of contracting cancer, inflammation, neurodegeneration diseases and/or diabetes, or reducing the severity of cancer, inflammation, neurodegeneration diseases and/or diabetes.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofurnayl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Inhibition of the generation of Factor XIa is a useful mean of anticoagulant therapy that can be achieved by inhibition of the activation of zymogen Factor XI. Factor XI activation inhibitors are useful anticoagulants not only in individuals having thrombotic conditions but are useful whenever inhibition of blood coagulation is required such as to prevent coagulation of stored whole blood and to prevent coagulation in other biological samples for testing or storage. Thus, the Factor XI activation inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used.

Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XI activation inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XI activation inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XI activation inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of Formula I can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XI activation inhibitors can also be co-administered with suitable anticoagulants, including, but not limited to, factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XI Activation Inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoAreductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XI activation inhibitors of the invention in combination with other suitable anti-platelet agents, anticoagulation agents, or thrombolytic agents may be the same as those doses of Factor XI activation inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

General Methods

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are carried out by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

For purposes of this specification, the following abbreviations have the indicated meanings:

| | |
|---|---|
| Ac | acetyl |
| ACN | acetonitrile |
| AcOH or HOAc | acetic acid |

| | |
|---|---|
| aq | aqueous |
| Bn | benzyl |
| Boc or BOC | tert-butoxycarbonyl |
| Bu | butyl |
| Bz | benzoyl |
| cBu | cyclobutyl |
| Cbz | benyzloxycarbonyl |
| cPr | cyclopropyl |
| d | double |
| DAST | (diethylamino)sulfur trifluoride |
| dba | dibenzylideneacetone |
| DCE | 1,2-dichloroethane |
| DCM | dichloromethane |
| DIBAL or Dibal-H | diisobutylaluminum hydride |
| DIEA, DIPEA or Hünig's base | N,N-diisopropylethylamine |
| DMA | 1,2-dimethylacetamide |
| DMAP | 4-dimethylaminopyridine |
| DMF | dimethylformamide |
| DMP | Dess-Martin periodinane (1,1,1-triacetoxy)-1,1-dihydro-1,2-benziodoxol-3(1H)-one |
| DMSO | dimethyl sulfoxide |
| dppf | 1,1'-bis(diphenylphosphino)ferrocene |
| EDC | 1-ethyl-3-(3-dimethylaminopropyl)carbodiimide |
| ESI | electrospray ionization |
| Et | ethyl |
| EtOH | ethanol |
| EtOAc | ethyl acetate |
| g | grams |
| h | hour |
| HATU | N,N,N',N;-tetramethyl-O-(7-azabenzotriazol-1-yl)uronium hexafluorophosphate |
| HMDS | 1,1,1,3,3,3-hexamethyldisilazane |
| HOBt | 1-hydroxybenzotriazole |
| HPLC | high-performance liquid chromatography |
| Hz | Hertz |
| IPA | isopropanol |
| iPr | isopropyl |
| LCMS, LC/MS | liquid chromatography mass spectrometry |
| L | liter |
| LDA | lithium diisopropylamide |
| LHMDS, LiHMDS | lithium bis(trimethylsilyl)amide |
| mCPBA | m-choroperoxybenzoic acid |
| m/z | mass-to-charge ratio |
| Me | methyl |
| MeOH | methanol |
| mg | milligrams |
| MHz | megahertz |
| min | minute |
| μL | microliters |
| mL | milliliters |
| mmol | millimoles |
| MS | mass spectrometry |
| Ms | methanesulfonyl (mesyl) |
| MTBE | methyl tert-butyl ether |
| M | Molar |
| NBS | N-bromosuccinimide |
| NMR | nuclear magnetic resonance spectroscopy |
| Ph | phenyl |
| PMB | p-methoxybenzyl |
| Pr | propyl |
| psi | pounds per square inch |
| rac | racemic mixture |
| RT or rt | room temperature (ambient, about 25° C.) |
| SEM | 2-(trimethylsilyl)ethoxy)methyl |
| SEM-Cl | (2-(chloromethoxy)ethyl)trimethylsilane |
| SFC | supercritical fluid chromatography |
| TBAF | tert-butyl ammonium fluoride |
| TBS or TBDMS | tert-butyldimethyl silyl |
| TBSCl | tert-butyldimethylsilyl chloride |
| TBDPS | tert-butyldiphenylsilyl |
| TBDPSCl | tert-butyldiphenylsilyl chloride |
| tBu | tert-butyl |
| tBu X-phos | 2-di-tert-butylphosphino-2',4',6'-triisopropylbiphenyl |
| TEA | triethylamine (Et$_3$N) |
| Tf | Triflate |
| TFA | trifluoroacetic acid |
| TFAA | trifluoroacetic anhydride |
| THF | THF |
| TLC | thin layer chromatography |
| TMS | trimethyl silyl |
| Tris | tris(hydroxymethyl)aminomethane |
| Ts | toluenesulfonyl (tolyl) |
| TSA | p-toluenesulfonic acid |
| X-phos | 2-dicyclohexylphosphino-2',4',6'-triisopropylbiphenyl |
| Xantphos | 4,5-bis(diphenylphosphino)-9,9-dimethylxanthene |
| Zhan catalyst | 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride |

General Scheme

Compounds of the present invention may be prepared using conventional techniques or according to the methodology outlined in the following general synthetic schemes.

General synthesis of multiple embodiments of the present invention are summarized in Scheme 1 which depicts the preparation of compounds I from intermediate 1a. Amide coupling of an excess of 1a with a cyclic amine using a reagent such as N,N,N,N'-tetramethyl-O-(7-azabenzotriazol-1-yl)uronium hexafluorophosphate (HATU) provides 1b. A second amide coupling of 1b with an amine utilizing a reagent such as HATU provides bis-amide 1c. Removal of the C6 protecting group, such as a para-chlorobenzyl, with a catalyst such as Pd/C provides free alcohol 1d. Alkylation of 1d with a benzylic halide or activated benzylic hydroxyl to provide 1.

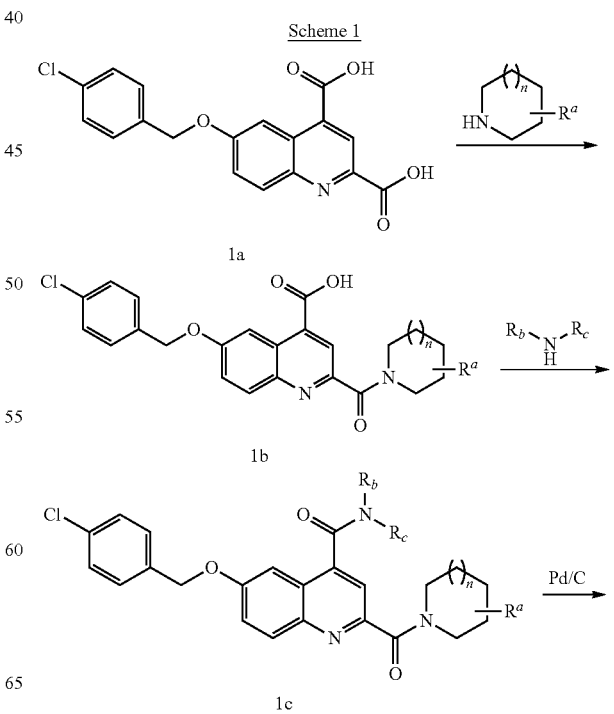

Scheme 1

-continued

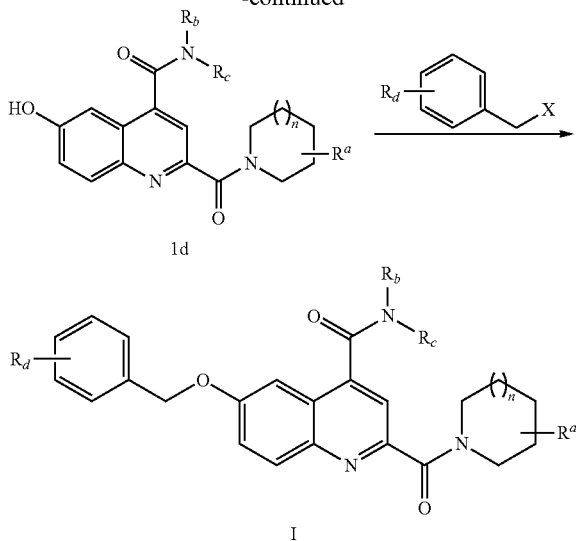

Intermediates

Intermediate 1

6-((4-chlorobenzyl)oxy)quinoline-2,4-dicarboxylic Acid

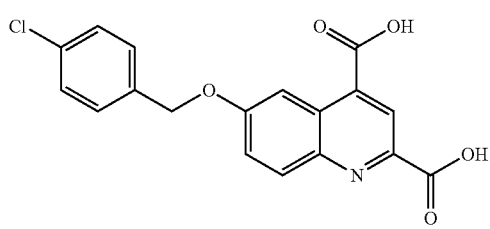 [SMILES: O=C(O)c1cc(C(=O)O)c2cc(OCc3ccc(Cl)cc3)ccc2n1]

Step A: 1-chloro-4-((4-nitrophenoxy)methyl)benzene

Into a 10-L round-bottom flask was placed 4-nitrophenol (200 g, 1.44 mol, 1.00 equiv), 1-(bromomethyl)-4-chlorobenzene (325 g, 1.58 mol, 1.10 equiv) and $K_2CO_3$ (1985 g, 14.38 mol, 5.00 equiv), which was suspended in dimethylformamide (2 L). The resulting solution was stirred for 6 h at 30° C. The reaction mixture was cooled with a water/ice bath. The resulting solution was extracted with ethyl acetate and the organic layers were combined. The solids were collected by filtration. The solid was dried in an oven under reduced pressure to provide 1-[(4-chlorophenyl)methoxy]-4-nitrobenzene.

Step B: 4-((4-chlorobenzyl)oxy)aniline

Into a 10-L 4-necked round-bottom flask was placed a solution of 1-[(4-chlorophenyl)methoxy]-4-nitrobenzene (240 g, 910.21 mmol, 1.00 equiv) in MeOH (4700 mL). Then Zn (1000 g, 20 equiv), HCl (6 M) (328 mL, 10 equiv), and $H_2O$ (4800 mL) were added. The resulting solution was stirred for 24 h at room temperature. The resulting solution was concentrated and washed with water. The solid was collected by filtration to provide 4-[(4-chlorophenyl)methoxy]aniline.

Step C: diethyl 6-((4-chlorobenzyl)oxy)quinoline-2,4-dicarboxylate

Into a 5-L 4-necked round-bottom flask was placed a solution of 4-[(4-chlorophenyl)methoxy]aniline (144 g, 616.19 mmol, 1.00 equiv) in ACN (2500 mL), ethyl 2-oxopropanoate (107 g, 921.50 mmol, 1.50 equiv), ethyl 2-oxoacetate (two portions: 62 g, 607.32 mmol, 1.00 equiv followed by 8.3 g, 0.05 equiv). The resulting solution was stirred for 3 h at 40° C. in an oil bath. The reaction mixture was cooled with a water/ice bath. The solids were collected by filtration. The solid was dried in an oven under reduced pressure to provide 2,4-diethyl 6-[(4-chlorophenyl)methoxy]quinoline-2,4-dicarboxylate.

Step D: 6-((4-chlorobenzyl)oxy)quinoline-2,4-dicarboxylic acid

Into a 5-L 4-necked round-bottom flask was placed a solution of 2,4-diethyl 6-[(4-chlorophenyl)methoxy]quinoline-2,4-dicarboxylate (72 g, 173.98 mmol, 1.00 equiv) in tetrahydrofuran (1500 mL) and a solution of lithium hydroxide (24 g, 1.00 mol, 6.00 equiv) in water (1500 mL). The resulting solution was stirred for 30 min at 30° C. in an oil bath. The pH value of the solution was adjusted to 1 with hydrogen chloride (1 M). The solids were collected by filtration to provide 6-[(4-chlorophenyl)methoxy]quinoline-2,4-dicarboxylic acid. MS (ES$^+$) m/z: 357.9 (M+H)

Intermediate 2

6-((4-chlorobenzyl)oxy)-4-(piperidine-1-carbonyl)quinoline-2-carboxylic Acid

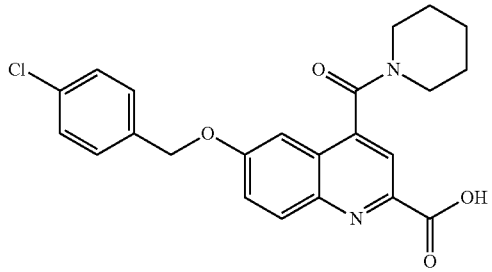 [SMILES: O=C(O)c1cc(C(=O)N2CCCCC2)c2cc(OCc3ccc(Cl)cc3)ccc2n1]

Step A: benzyl 2-oxopropanoate

Into a 5-L 4-necked round-bottom flask was placed a solution of 2-oxopropanoic acid (194 g, 1 equiv) in THF (2 L), BnOH (357 g, 1.5 equiv), Pyridine (348 g, 2 equiv) and MsCl (504 g, 2 equiv). The resulting solution was stirred for 16 h at 15° C. The reaction was then quenched by the addition of water. The resulting solution was extracted with ethyl acetate and the organic layer was combined. The resulting mixture was washed with brine. The resulting mixture was concentrated to provide benzyl 2-oxopropanoate.

Step B: 4-benzyl 2-ethyl 6-hydroxyquinoline-2,4-dicarboxylate

Into a 5-L 4-necked round-bottom flask was placed a solution of 4-aminophenol (100.6 g, 1 equiv) in ACN (2 L). Benzyl 2-oxopropanoate (212 g, 1.29 equiv), ethyl 2-oxoacetate (94 g, 1 equiv), and $I_2$ (11.7 g, 0.05 equiv) were added. The resulting solution was stirred for 4 h at 40° C. in an oil bath. The reaction mixture was cooled to 15° C. with a water/ice bath. The solids were collected by filtration. The solid was washed with MTBE 3 times and dried in an oven under reduced pressure to provide 4-benzyl 2-ethyl 6-hydroxyquinoline-2,4-dicarboxylate.

Step C: 2-(ethoxycarbonyl)-6-hydroxyquinoline-4-carboxylic acid

Into a 2-L 3-necked round-bottom flask was placed a solution of 4-benzyl 2-ethyl 6-hydroxyquinoline-2,4-dicarboxylate (109 g, 1 equiv) in THF (1 L). Pd(OH)$_2$/C (18 g, 0.08 equiv), and H$_2$ were added. The resulting solution was stirred for 1 h at 15° C. The reaction was then quenched by the addition of water. The solids were collected by filtration. The solid was washed with THF. The solid was dried in an oven under reduced pressure to provide 2-(ethoxycarbonyl)-6-hydroxyquinoline-4-carboxylic acid.

Step D: ethyl 6-hydroxy-4-(piperidine-1-carbonyl)quinoline-2-carboxylate

Into a 2-L 3-necked round-bottom flask was placed a solution of 2-(ethoxycarbonyl)-6-hydroxyquinoline-4-carboxylic acid (71 g, 1 equiv) in DMF (710 mL). Piperidine (27 g, 1.2 equiv), DIEA (175 g, 5 equiv), and HATU (124 g, 1.2 equiv) were added. The resulting solution was stirred for 4 h at 15° C. The reaction was then quenched by the addition of water. The resulting solution was extracted with dichloromethane and the organic layer was combined. The resulting mixture was washed with brine. The mixture was dried over anhydrous sodium sulfate and concentrated to provide ethyl 6-hydroxy-4-[(piperidin-1-yl)carbonyl]quinoline-2-carboxylate.

Step E: ethyl 6-((4-chlorobenzyl)oxy)-4-(piperidine-1-carbonyl)quinoline-2-carboxylate Into a 1-L 3-necked round-bottom flask was placed a solution of ethyl 6-hydroxy-4-[(piperidin-1-yl)carbonyl]quinoline-2-carboxylate (56.6 g, 1 equiv) in DMF (500 mL). 1-(bromomethyl)-4-chlorobenzene (53 g, 1.5 equiv) and K$_2$CO$_3$ (71 g, 3 equiv) were added. The resulting solution was stirred for 2 h at 20° C. The reaction was then quenched by the addition of water. The solids were collected by filtration and washed with water. The solid was dried in an oven under reduced pressure to provide ethyl 6-[(4-chlorophenyl)methoxy]-4-[(piperidin-1-yl)carbonyl]quinoline-2-carboxylate.

Step F: 6-((4-chlorobenzyl)oxy)-4-(piperidine-1-carbonyl)quinoline-2-carboxylic acid Into a 2-L 3-necked round-bottom flask was placed a solution of ethyl 6-[(4-chlorophenyl)methoxy]-4-[(piperidin-1-yl)carbonyl]quinoline-2-carboxylate (59.3 g, 1 equiv) in THF (500 mL). A solution of lithium hydroxide (9.4 g, 3 equiv) in H$_2$O (500 mL) was added. The resulting solution was stirred for 30 min at room temperature. The resulting mixture was concentrated. The solids were collected by filtration washed with DCM. The solid was dried in an oven under reduced pressure to provide 6-[(4-chlorophenyl)methoxy]-4-[(piperidin-1-yl)carbonyl]quinoline-2-carboxylic acid. MS (ES$^+$) m/z: 425 (M+H)

Intermediate 3

6-(benzo[d]thiazol-2-ylmethoxy)-4-(piperidine-1-carbonyl)quinoline-2-carboxylic acid

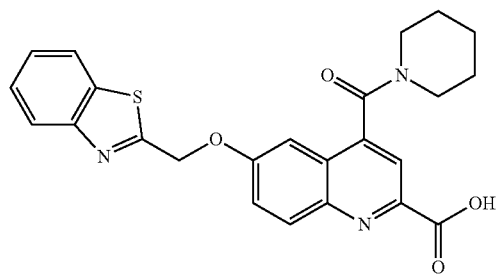 [SMILES: O=C(O)c1cc(C(=O)N2CCCCC2)c2cc(OCc3nc4ccccc4s3)ccc2n1]

Step A: 4-benzyl 2-ethyl 6-hydroxyquinoline-2,4-dicarboxylate 4-aminophenol (90 g, 824.7 mmol, 128.6 mL, 1.0 eq) and ACN (630 mL) were added to a three-neck bottle at 15° C. under N$_2$. Benzyl 2-oxopropanoate (190 g, 1.07 mol, 212.8 mL, 1.29 eq) and ethyl 2-oxoacetate (168.4 g, 824.7 mmol, 1 eq) were added to the reaction mixture at 15° C. I$_2$ (10.5 g, 41.2 mmol, 8.3 mL, 0.05 eq) was added to the reaction mixture in one portion at 15° C. The mixture was heated to 40° C. and stirred for 4 h and confirmed it was complete by TLC. The reaction mixture was cooled to 15 C, filtered, and washed with MTBE. The filter cake was dried in a vacuum to provide 4-benzyl 2-ethyl 6-hydroxyquinoline-2,4-dicarboxylate. MS (ES$^+$) m/z: 352 (M+H)

Step B: 2-(ethoxycarbonyl)-6-hydroxyquinoline-4-carboxylic acid 4-benzyl 2-ethyl 6-hydroxyquinoline-2,4-dicarboxylate (60 g, 170.8 mmol, 1.0 eq) was added to THF (600 mL) in a hydrogenated bottle at 15° C. Pd(OH)$_2$ (10 g, 14.2 mmol, 20% purity, 0.08 eq) was added to the mixture in one portion at 15° C. and the mixture was charged with H$_2$. The mixture was stirred 15° C. for 1 h under H$_2$ (50 psi). The mixture was cooled to 15° C. then filtered through a Celite pad, and washed with THF. The filtrate was dried a in vacuum to provide a residue. EtOAc to the residue and it was stirred for 20 min. The mixture was filtered and dried in a vacuum to provide 2-(ethoxycarbonyl)-6-hydroxyquinoline-4-carboxylic acid. MS (ES$^+$) m/z: 262 (M+H)

Step C: ethyl 6-hydroxy-4-(piperidine-1-carbonyl)quinoline-2-carboxylate 2-(Ethoxycarbonyl)-6-hydroxyquinoline-4-carboxylic acid (42 g, 160.8 mmol, 1.0 eq) and piperidine (13.7 g, 160.8 mmol, 15.9 mL, 1 eq), were dissolved in DMF (294 mL) in a three-neck bottle at 15° C. under N$_2$. DIEA (41.6 g, 321.6 mmol, 56 mL, 2.0 eq), followed by HATU (73.4 g, 192.9 mmol, 1.2 eq), were added to the reaction mixture at 0-5° C. The mixture was stirred at 15° C. for 4 h. The reaction was determined to be complete by TLC. The mixture was poured into cold $H_2O$ (500 mL) then stirred for 10 min. The mixture was extracted with DCM (200 mL), washed with brine (200 mL), dried over $Na_2SO_4$, filtered and evaporated to provide ethyl 6-hydroxy-4-(piperidine-1-carbonyl)quinoline-2-carboxylate. MS ($ES^+$) m/z: 329 (M+H)

Step D: ethyl 6-(benzo[d]thiazol-2-ylmethoxy)-4-(piperidine-1-carbonyl)quinoline-2-carboxylate Ethyl 6-hydroxy-4-(piperidine-1-carbonyl)quinoline-2-carboxylate (52 g, 158.4 mmol, 1.0 eq) and 2-(bromomethyl)benzo[d]thiazole (36.1 g, 158.4 mmol, 1.0 eq) were added to DMF (360 mL) in a three-neck bottle at 15° C. under $N_2$. $K_2CO_3$ (65.7 g, 475.1 mmol, 3.0 eq) was added to the reaction mixture in one portion at 15° C. under $N_2$. The mixture was stirred at 20° C. for 2 h. The reaction was determined to be complete by TLC. The reaction mixture was poured into $H_2O$ then stirred for 10 min. The mixture was filtered and washed with $H_2O$ and dried in vacuum to obtain ethyl 6-(benzo[d]thiazol-2-ylmethoxy)-4-(piperidine-1-carbonyl)quinoline-2-carboxylate. MS ($ES^+$) m/z: 476 (M+H)

Step E: 6-(benzo[d]thiazol-2-ylmethoxy)-4-(piperidine-1-carbonyl)quinoline-2-carboxylic acid Ethyl 6-(benzo[d]thiazol-2-ylmethoxy)-4-(piperidine-1-carbonyl)quinoline-2-carboxylate (50 g, 105.1 mmol, 1.0 eq) was dissolved in THF (350 mL) and $H_2O$ (350 mL) in a three-neck bottle at 15° C. under $N_2$. $LiOH·H_2O$ (8.8 g, 210.3 mmol, 2.0 eq) was added to the mixture in one portion at 15° C. The mixture was stirred at 15° C. for 1 h then concentrated to remove THF. The pH of the aqueous layer was adjusted to 1 with 1N HCl. The mixture was filtered, washed with $H_2O$, and dried in vacuum to give the crude product. MTBE was added to the crude product and stirred for 30 min. The mixture was washed with MTBE to obtain 6-(benzo[d]thiazol-2-ylmethoxy)-4-(piperidine-1-carbonyl)quinoline-2-carboxylic acid. MS ($ES^-$) m/z: 446(M−H)

Intermediate 4

2-(4-(1H-pyrazol-1-yl)piperidine-1-carbonyl)-6-(benzo[d]thiazol-2-ylmethoxy)quinoline-4-carboxylic acid

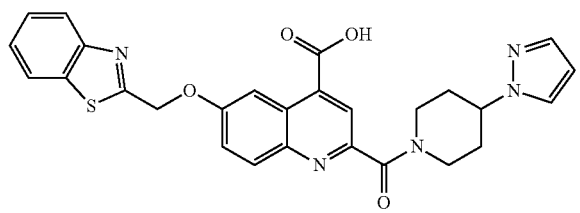 [SMILES: O=C(O)c1cc(C(=O)N2CCC(n3cccn3)CC2)nc2ccc(OCc3nc4ccccc4s3)cc12]

Step A: diethyl 6-hydroxyquinoline-2,4-dicarboxylate

Into a 3-L 4-necked round-bottom flask was placed a solution of 4-aminophenol (167 g, 1.53 mol, 1.00 equiv) in ACN (1600 mL), ethyl 2-oxopropanoate (267 g, 2.30 mol, 1.50 equiv), ethyl 2-oxoacetate (312 g, 3.06 mol, 1.00 equiv), and $FeCl_3·6H_2O$ (20 g, 74.07 mmol, 0.05 equiv). The resulting solution was stirred for 5 h at 40° C. in an oil bath. The reaction mixture was cooled with a water/ice bath. The solids were collected by filtration. The solid was dried in an oven under reduced pressure to provide diethyl 6-hydroxyquinoline-2,4-dicarboxylate.

Step B: diethyl 6-(benzo[d]thiazol-2-ylmethoxy) quinoline-2,4-dicarboxylate

Into a 5-L 4-necked round-bottom flask was placed a solution of 2,4-diethyl 6-hydroxyquinoline-2,4-dicarboxylate (222 g, 767.41 mmol, 1.00 equiv) in N,N-dimethylformamide (2500 mL). 2-(bromomethyl)-1,3-benzothiazole (262 g, 1.15 mol, 1.50 equiv), $Cs_2CO_3$ (500 g, 1.53 mol, 2.00 equiv) were added. The resulting solution was stirred for 6 h at 30° C. in an oil bath. The reaction was then quenched by the addition of water. The solids were collected by filtration. The solid was dried in an oven under reduced pressure to provide 2,4-diethyl 6-(1,3-benzothiazol-2-ylmethoxy)quinoline-2,4-dicarboxylate.

Step C: 6-(benzo[d]thiazol-2-ylmethoxy)quinoline-2,4-dicarboxylic acid

Into a 5-L 4-necked round-bottom flask, was placed a solution of 2,4-diethyl 6-(1,3-benzothiazol-2-ylmethoxy) quinoline-2,4-dicarboxylate (168 g, 384.90 mmol, 1.00 equiv) in tetrahydrofuran (1500 mL). A solution of lithium hydroxide (55 g, 2.30 mol, 6.00 equiv) in water (1500 mL) was added. The resulting solution was stirred for 40 min at room temperature. The resulting mixture was concentrated under vacuum. The pH value of the solution was adjusted to 3 with 1M HCl. The solids were collected by filtration. The solid was dried in an oven under reduced pressure to provide 6-(1,3-benzothiazol-2-ylmethoxy)quinoline-2,4-dicarboxylic acid.

Step D: 2-(4-(1H-pyrazol-1-yl)piperidine-1-carbonyl)-6-(benzo[d]thiazol-2-ylmethoxy)quinoline-4-carboxylic acid Into a 2-L 3-necked round-bottom flask, was placed 4-(1H-pyrazol-1-yl)piperidine (38.2 g, 252.63 mmol, 0.50 equiv), a solution of 6-(1,3-benzothiazol-2-ylmethoxy)quinoline-2,4-dicarboxylic acid (125 g, 328.62 mmol, 1.00 equiv) in N,N-dimethylformamide (1200 mL), DIEA (106 g, 821.71 mmol, 2.50 equiv), and HATU (75 g, 197.37 mmol, 0.60 equiv). The resulting solution was stirred for 60 min at room temperature. The mixture was purified by reverse phase HPLC. The pH value of the solution was adjusted to pH 4 with 1M HCl. The solids were collected by filtration. The filtrate was extracted with dichloromethane and the organic layers combined and dried over anhydrous magnesium sulfate and concentrated under vacuum to provide 6-(1,3-benzothiazol-2-ylmethoxy)-2-[[4-(1H-pyrazol-1-yl)piperidin-1-yl]carbonyl]quinoline-4-carboxylic acid. MS ($ES^+$) m/z: 514 (M+H)

Intermediate 5

(4-(1H-pyrazol-1-yl)piperidin-1-yl)(6-hydroxy-4-(piperidine-1-carbonyl)quinolin-2-yl)methanone

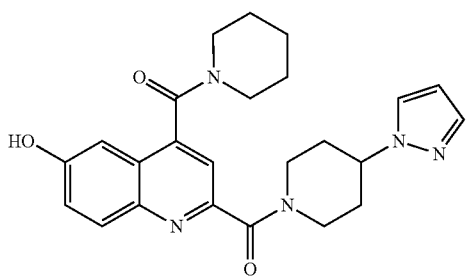 [SMILES: O=C(c1cc(C(=O)N2CCCCC2)c2cc(O)ccc2n1)N1CCC(n2cccn2)CC1]

Step A: 6-hydroxy-4-(piperidine-1-carbonyl)quinoline-2-carboxylic acid

Hydrogen bromide (2 ml, 12.15 mmol) was added to 6-((4-chlorobenzyl)oxy)-4-(piperidine-1-carbonyl)quinoline-2-carboxylic acid (333.4 mg, 0.785 mmol) and the mixture was stirred at 60° C. overnight. LCMS showed the reaction was complete. The mixture was cooled, water was added and the mixture was extracted with ethyl acetate. The combined organic fractions were evaporated under reduced pressure to afford 6-hydroxy-4-(piperidine-1-carbonyl)quinoline-2-carboxylic acid. MS (ES$^+$) m/z: 301 (M+H)

Step B: (4-(1H-pyrazol-1-yl)piperidin-1-yl)(6-hydroxy-4-(piperidine-1-carbonyl)quinolin-2-yl)methanone HATU (349 mg, 0.919 mmol) was added to a stirred mixture of 6-hydroxy-4-(piperidine-1-carbonyl)quinoline-2-carboxylic acid (184 mg, 0.613 mmol), 4-(1H-pyrazol-1-yl)piperidine hydrochloride (142.2 mg, 0.758 mmol) and N,N-diisopropylethylamine (0.747 ml, 4.29 mmol) in DMF (5 ml) and the mixture was stirred at room temperature overnight. The reaction was filtered, the solution was purified by preparative HPLC Reverse phase (C-18), eluting with Acetonitrile/Water+0.1% TFA, to provide (4-(1H-pyrazol-1-yl)piperidin-1-yl)(6-hydroxy-4-(piperidine-1-carbonyl)quinolin-2-yl)methanone. MS (ES$^+$) m/z: 434 (M+H)

Intermediate 6

1-(6-hydroxy-4-(piperidine-1-carbonyl)quinoline-2-carbonyl)-4-phenylpiperidine-4-carbonitrile

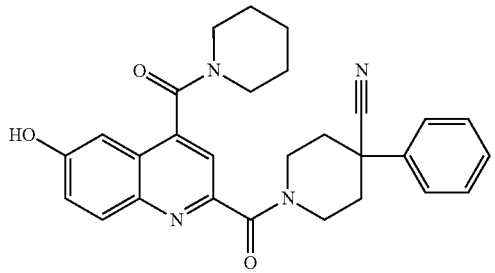 [SMILES: N#CC1(c2ccccc2)CCN(C(=O)c2cc(C(=O)N3CCCCC3)c3cc(O)ccc3n2)CC1]

Step A: 6-hydroxy-4-(piperidine-1-carbonyl)quinoline-2-carboxylic Acid

Hydrogen bromide (2 ml, 12.15 mmol) was added to 6-((4-chlorobenzyl)oxy)-4-(piperidine-1-carbonyl)quinoline-2-carboxylic acid (333.4 mg, 0.785 mmol) and the mixture was stirred at 60° C. overnight. The mixture was cooled, water was added, and the mixture was extracted with ethyl acetate. The combined organic fractions were evaporated under reduced pressure to afford 6-hydroxy-4-(piperidine-1-carbonyl)quinoline-2-carboxylic acid. MS (ES$^+$) m/z: 301 (M+H)

Step B: 1-(6-hydroxy-4-(piperidine-1-carbonyl)quinoline-2-carbonyl)-4-phenylpiperidine-4-carbonitrile 2-(3H-[1,2,3]triazolo[4,5-b]pyridin-3-yl)-1,1,3,3-tetramethylisouronium hexafluorophosphate(V) (375 mg, 0.986 mmol) was added to a stirred mixture of 6-hydroxy-4-(piperidine-1-carbonyl)quinoline-2-carboxylic acid (148 mg, 0.493 mmol), 4-phenylpiperidine-4-carbonitrile hydrochloride (215 mg, 0.965 mmol) and DIPEA (0.861 ml, 4.93 mmol) in DMF (3 ml) and the mixture was stirred at room temperature overnight. 1M Hydrochloric acid was added and the mixture was extracted with ethyl acetate. The combined organic fractions were washed with brine, dried (Na$_2$SO$_4$), filtered and the solvent was evaporated under reduced pressure. The residue was purified by column chromatography on silica gel (eluting with 0-100% EtOAc in hexane) to give 1-(6-hydroxy-4-(piperidine-1-carbonyl)quinoline-2-carbonyl)-4-phenylpiperidine-4-carbonitrile. MS (ES$^+$) m/z: 469 (M+H)

Intermediate 7

Rac-(6-hydroxy-2-(3-hydroxy-3-methylpyrrolidine-1-carbonyl)quinolin-4-yl)(piperidin-1-yl)methanone

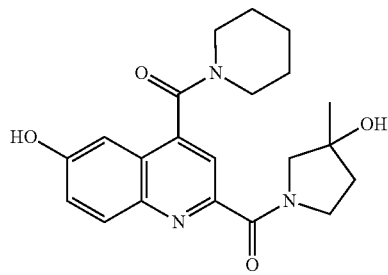 [SMILES: CC1(O)CCN(C(=O)c2cc(C(=O)N3CCCCC3)c3cc(O)ccc3n2)C1]

Step A. (6-((4-chlorobenzyl)oxy)-2-(3-hydroxy-3-methylpyrrolidine-1-carbonyl)quinolin-4-yl)(piperidin-1-yl)methanone To a solution of 6-((4-chlorobenzyl)oxy)-4-(piperidine-1-carbonyl)quinoline-2-carboxylic acid (250 mg, 0.588 mmol) and 3-methylpyrrolidin-3-ol (89 mg, 0.883 mmol) in DMF (3 mL) was added HATU (336 mg, 0.883 mmol) and triethylamine (179 mg, 1.765 mmol). Then the mixture was stirred for 2 h. Saturated aq. NaHCO$_3$ was added into the reaction mixture and it was extracted with DCM. The combined organic layers were washed with brine and concentrated to give (6-((4-chlorobenzyl)oxy)-2-(3-hydroxy-3- methylpyrrolidine-1-carbonyl)quinolin-4-yl)(piperidin-1-yl)methanone. MS (ES+) m/z: 508.0 (M+H)

Step B. (6-hydroxy-2-(3-hydroxy-3-methylpyrrolidine-1-carbonyl)quinolin-4-yl)(piperidin-1-yl)methanone To a degassed solution of (6-((4-chlorobenzyl)oxy)-2-(3-hydroxy-3-methylpyrrolidine-1-carbonyl)quinolin-4-yl)(piperidin-1-yl)methanone (400 mg, 0.598 mmol) in MeOH (30 mL) was added Pd/C (10%, 127 mg, 0.120 mmol) at 20° C. The resulting mixture was stirred at 20° C. for 24 h under H₂ (15 psi). The mixture was filtered and the filtrate was concentrated to give (6-hydroxy-2-(3-hydroxy-3-methylpyrrolidine-1-carbonyl)quinolin-4-yl)(piperidin-1-yl)methanone. MS (ESI) m/z 384.1 (M+H)

Intermediate 8

4-(1H-pyrazol-1-yl)piperidine-4-carbonitrile

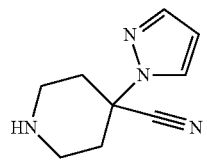 [SMILES: N#CC1(n2cccn2)CCNCC1]

Step A. 1-(tert-butoxycarbonyl)-4-(1H-pyrazol-1-yl)piperidine-4-carboxylic acid

To a solution of 1H-pyrazole (1 g, 14.69 mmol) in THF (10 mL) was added sodium hydroxide (2.94 g, 73.4 mmol) and tert-butyl 4-oxopiperidine-1-carboxylate (5.85 g, 29.4 mmol) at 0° C. Then chloroform (8.77 g, 73.4 mmol) was added and the mixture was stirred at 0° C. for 1 h and at 15° C. for 15 h. The reaction was filtered, the filter cake was diluted with water, and washed with MTBE. Citric acid (1 M) was added into the aqueous phase until pH=3 and it was extracted with EtOAc. The combined organic layers were washed by brine, dried over anhydrous Na₂SO₄ and concentrated to give 1-(tert-butoxycarbonyl)-4-(1H-pyrazol-1-yl)piperidine-4-carboxylic acid.

Step B. tert-butyl 4-carbamoyl-4-(1H-pyrazol-1-vi)piperidine-1-carboxylate

To a solution of 1-(tert-butoxycarbonyl)-4-(1H-pyrazol-1-yl)piperidine-4-carboxylic acid (500 mg, 1.693 mmol), ammonium chloride (317 mg, 5.93 mmol) in DMF (7 mL) was added HATU (966 mg, 2.54 mmol) and triethylamine (0.590 mL, 4.23 mmol). The reaction mixture was stirred at 15° C. for 2 h. Water was added into the reaction mixture and it was extracted with EtOAc. The combined organic layers were washed with saturated aq. NaHCO₃, followed by concentration to give tert-butyl 4-carbamoyl-4-(1H-pyrazol-1-yl)piperidine-1-carboxylate which was used directly without further purification. MS (ES+) m/z: 239.1 (M-56+H)

Step C. tert-butyl 4-cyano-4-(1H-pyrazol-1-yl)piperidine-1-carboxylate

To a solution of tert-butyl 4-carbamoyl-4-(1H-pyrazol-1-yl)piperidine-1-carboxylate (250 mg, 0.849 mmol) in DCM (6 mL) was added triethylamine (0.355 mL, 2.55 mmol). Then TFAA (0.180 mL, 1.274 mmol) was added at 0° C. The reaction mixture was stirred at 15° C. for 5 h. LCMS showed the reaction was almost complete. Water (5 mL) was added into the reaction mixture and it was extracted with EtOAc (5 mL×3). The combined organic layers were concentrated to give a residue. The residue was purified by Prep-TLC (EtOAc) to give tert-butyl 4-cyano-4-(1H-pyrazol-1-yl)piperidine-1-carboxylate. MS (ESI) m/z 221 (M-56+H)

Step D. 4-(1H-pyrazol-1-yl)piperidine-4-carbonitrile

To a solution of tert-butyl 4-cyano-4-(1H-pyrazol-1-yl)piperidine-1-carboxylate (110 mg, 0.398 mmol) in DCM (3 mL) was added TFA (0.613 mL, 7.96 mmol) at 0° C. Then the reaction mixture was stirred at 15° C. for 3 h. The reaction was concentrated to give 4-(1H-pyrazol-1-yl)piperidine-4-carbonitrile which was used directly without further purification. MS (ESI) m z 177.0 (M+H)

Intermediate 9

1-(6-hydroxy-4-(piperidine-1-carbonyl)quinoline-2-carbonyl)-4-(1H-pyrazol-1-yl)piperidine-4-carbonitrile

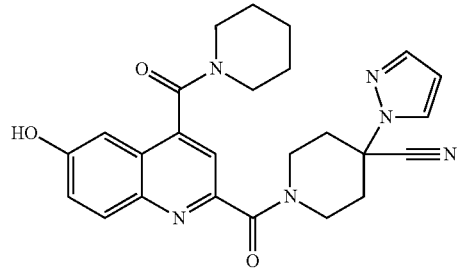 [SMILES: N#CC1(n2cccn2)CCN(C(=O)c2cc(C(=O)N3CCCCC3)c3cc(O)ccc3n2)CC1]

Step A. 1-(6-((4-chlorobenzyl)oxy)-4-(piperidine-1-carbonyl)quinoline-2-carbonyl)-4-(H-pyrazol-1-yl)piperidine-4-carbonitrile To a solution of 6-((4-chlorobenzyl)oxy)-4-(piperidine-1-carbonyl)quinoline-2-carboxylic acid (300 mg, 0.706 mmol) and 4-(1H-pyrazol-1-yl)piperidine-4-carbonitrile (187 mg, 1.059 mmol) in DCM (3 mL) was added HATU (403 mg, 1.059 mmol) and triethylamine (71.4 mg, 0.706 mmol). Then DMF (1 mL) was added. The reaction mixture was stirred at 15° C. for 2 h. Saturated aq. NaHCO₃ was added into the reaction mixture and it was extracted with DCM. The combined organic layers were washed with brine and concentrated to give 1-(6-((4-chlorobenzyl)oxy)-4-(piperidine-1-carbonyl)quinoline-2-carbonyl)-4-(1H-pyrazol-1-yl)piperidine-4-carbonitrile. MS (ESI) m/z 583.2 (M+H)

Step B. 1-(6-hydroxy-4-(piperidine-1-carbonyl)quinoline-2-carbonyl)-4-(1H-pyrazol-1-yl)piperidine-4-carbonitrile A solution of 1-(6-((4-chlorobenzyl)oxy)-4-(piperidine-1-carbonyl)quinoline-2-carbonyl)-4-(1H-pyrazol-1-yl)piperidine-4-carbonitrile (250 mg, 0.429 mmol) in TFA (4 mL) was stirred at 80° C. for 12 h. LCMS showed the reaction was complete. The reaction mixture was concentrated, the residue was diluted with water and it was extracted with EtOAc. The combined organic layers were dried over anhydrous Na₂SO₄, followed by concentration and purified by column chromatography on silica gel (eluting with 0-25% ethyl acetate in petroleum ether) to give 1-(6-hydroxy-4-(piperidine-1-carbonyl)quinoline-2-carbonyl)-4-(1H-pyrazol-1-yl)piperidine-4-carbonitrile. MS (ESI) m/z 459.2 (M+H)

Intermediate 10

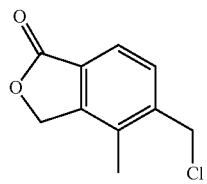

Step A. 4-methyl-5-vinylisobenzofuran-1(3H)-one

To a degassed solution of 4-methyl-1-oxo-1,3-dihydroisobenzofuran-5-yl trifluoromethanesulfonate (1 g, 3.38 mmol), TEA (0.941 mL, 6.75 mmol) and potassium vinyltrifluoroborate (0.904 g, 6.75 mmol) in EtOH (10 mL) was added Pd(dppf)Cl₂ (0.247 g, 0.338 mmol) at 25° C. under N₂ protection. The resulting mixture was heated to 90° C. for 12 h. The mixture was diluted with DCM and water, and filtered through a Celite pad. The filtrate was separated, and the aqueous phase was extracted with DCM. The combined organic layers were washed with water and brine, dried over anhydrous Na₂SO₄, filtered and concentrated, and the crude product was purified by column chromatography on silica gel (eluting with 1-5% ethyl acetate in petroleum ether) to give 4-methyl-5-vinylisobenzofuran-1(3H)-one. MS (ESI) m/z 175.1 (M+H)

Step B. 4-methyl-1-oxo-1,3-dihydroisobenzofuran-5-carbaldehyde

To a solution of 4-methyl-5-vinylisobenzofuran-1(3H)-one (1.3 g, 7.46 mmol) in acetone (15 mL) and water (15 mL) was added potassium osmate(VI) dihydrate (0.110 g, 0.299 mmol) at 20° C. The mixture was stirred for 10 min, then sodium periodate (6.38 g, 29.9 mmol) was added by portions, and the reaction temperature was maintained below 40° C. using an ice-bath, and the resulting mixture was stirred for 1 h. The suspension was filtered, and the filtrate was diluted with water and extracted with EtOAc. The combined organic layers were washed with water and brine, dried over anhydrous Na₂SO₄, filtered and concentrated to give 4-methyl-1-oxo-1,3-dihydroisobenzofuran-5-carbaldehyde which was carried to the next step without further purification.

Step C. 5-(hydroxymethyl)-4-methylisobenzofuran-1(3H)-one

To a solution of 4-methyl-1-oxo-1,3-dihydroisobenzofuran-5-carbaldehyde (1.1 g, 6.24 mmol) in MeOH (10 mL) was added NaBH₄ (0.236 g, 6.24 mmol) at 20° C., and the mixture was stirred at 20° C. for 1 h. The mixture was diluted with saturated aq. NH₄Cl, extracted with EtOAc, the combined organic layers were washed with water and brine, dried over anhydrous Na₂SO₄, filtered and concentrated to give 5-(hydroxymethyl)-4-methylisobenzofuran-1(3H)-one which was carried to the next step without further purification. MS (ESI) m/z 179.0 (M+H)

Step D. 5-(chloromethyl)-4-methylisobenzofuran-1(3H)-one

To a solution of 5-(hydroxymethyl)-4-methylisobenzofuran-1(3H)-one (900 mg, 5.05 mmol) in DCM (5 mL) was added SOCl₂ (1 mL, 13.70 mmol), followed by 2 drops of DMF. The mixture was stirred at 20° C. for 2 h and LCMS showed the reaction was complete. The mixture was concentrated, and the residue was dissolved in DCM, washed with saturated aq. NaHCO₃ and brine, dried over anhydrous Na₂SO₄, filtered and concentrated to give 5-(chloromethyl)-4-methylisobenzofuran-1(3H)-one. MS (ESI) m/z 197.0 (M+H)

EXAMPLES

Example 1

1-(6-((4-methyl-1-oxo-1,3-dihydroisobenzofuran-5-yl)methoxy)-4-(piperidine-1-carbonyl)quinoline-2-carbonyl)-4-(1H-pyrazol-1-yl)piperidine-4-carbonitrile

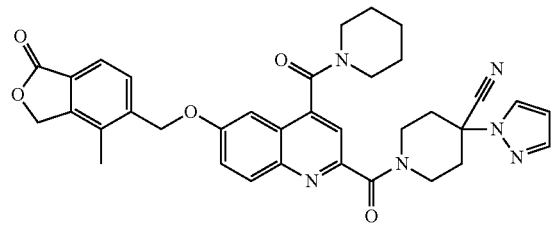 [SMILES: Cc1c(COc2ccc3nc(C(=O)N4CCC(C#N)(n5cccn5)CC4)cc(C(=O)N4CCCCC4)c3c2)ccc2c1COC2=O]

Synthetic Scheme

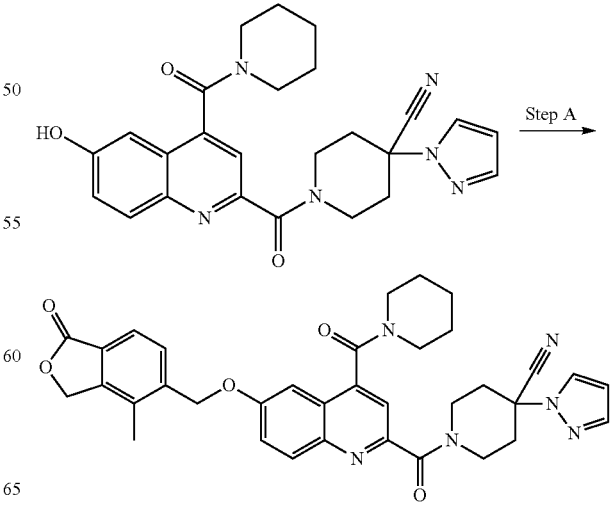

Step A. 1-(6-((4-methyl-1-oxo-1,3-dihydroisobenzofuran-5-yl)methoxy)-4-(piperidine-1-carbonyl)quinoline-2-carbonyl)-4-(1H-pyrazol-1-yl)piperidine-4-carbonitrile To a solution of 1-(6-hydroxy-4-(piperidine-1-carbonyl)quinoline-2-carbonyl)-4-(1H-pyrazol-1-yl)piperidine-4-carbonitrile (170 mg, 0.371 mmol) and 5-(chloromethyl)-4-methylisobenzofuran-1(3H)-one (87 mg, 0.445 mmol) in DMF (3 mL) was added K$_2$CO$_3$ (128 mg, 0.927 mmol) under N$_2$ in a schlenk flask. The reaction was stirred at 40° C. for 16 h. The mixture was purified by reversed phase HPLC to give 1-(6-((4-methyl-1-oxo-1,3-dihydroisobenzofuran-5-yl)methoxy)-4-(piperidine-1-carbonyl)quinoline-2-carbonyl)-4-(1H-pyrazol-1-yl)piperidine-4-carbonitrile. MS (ESI) m/z 619.2 (M+H)

By using the procedure described above and the appropriate starting materials, the following compound was synthesized and characterized by LC/MS.

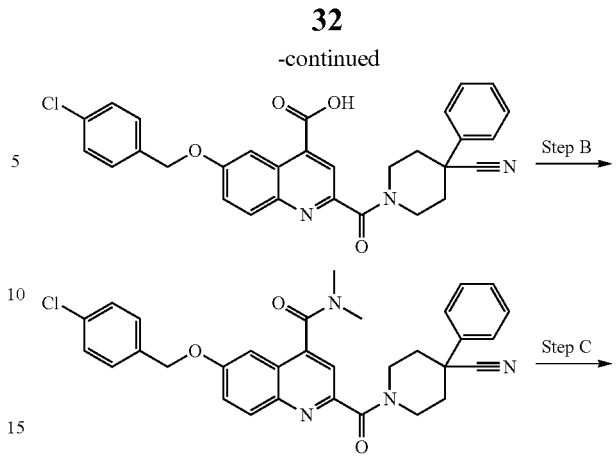

| Ex # | Structure | Name | Exact Mass [M + H]$^+$ |
|---|---|---|---|
| 2 | 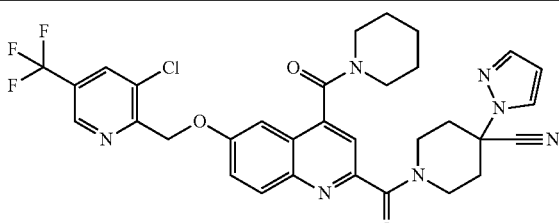 | 1-(6-((3-chloro-5-(trifluoromethyl)pyridin-2-yl)methoxy)-4-(piperidine-1-carbonyl)quinoline-2-carbonyl)-4-(1H-pyrazol-1-yl)piperidine-4-carbonitrile | 652.0 |

Example 3

1-(3-(benzo[d]thiazol-2-ylmethoxy)-5-(piperidine-1-carbonyl)isoquinoline-7-carbonyl)-4-phenylpiperidine-4-carbonitrile

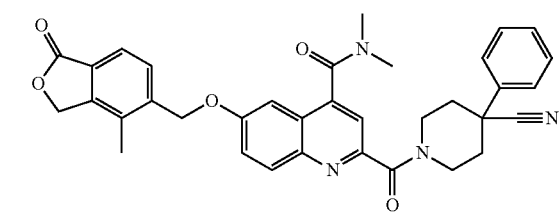 [SMILES: Cc1c(COc2ccc3nc(C(=O)N4CCC(C#N)(c5ccccc5)CC4)cc(C(=O)N(C)C)c3c2)ccc2c1COC2=O]

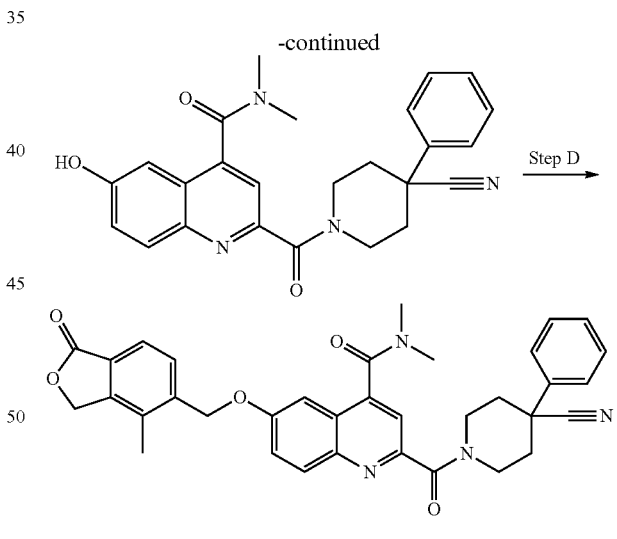

Synthetic Scheme

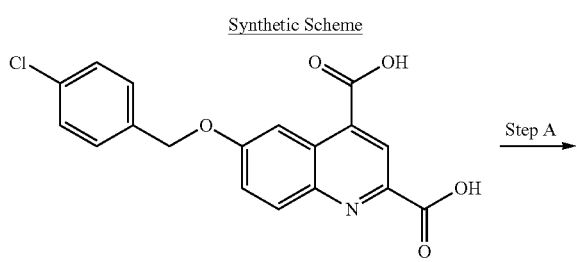

Step A. 6-((4-chlorobenzyl)oxy)-2-(4-cyano-4-phenylpiperidine-1-carbonyl)quinoline-4-carboxylic Acid To a stirred mixture of 6-((4-chlorobenzyl)oxy)quinoline-2,4-dicarboxylic acid (500 mg, 1.398 mmol) and 4-phenylpiperidine-4-carbonitrile hydrochloride (327 mg, 1.468 mmol) in DMSO (20 mL) was added DIEA (2.441 mL, 13.98 mmol), 2,4,6-tripropyl-1,3,5,2,4,6-trioxatriphosphinane 2,4,6-trioxide (2.404 mL, 2.80 mmol). The mixture was stirred at 30° C. for 16 h. Water was added to the mixture and the mixture was extracted by EtOAc, the combined organic layers were washed with brine and concentrated to give 6-((4-chlorobenzyl)oxy)-2-(4-cyano-4-phenylpiperidine-1-carbonyl)quinoline-4-carboxylic acid which was used directly without further purification. MS (ESI) m/z 526.1 (M+H)

Step B. 6-((4-chlorobenzyl)oxy)-2-(4-cyano-4-phenylpiperidine-1-carbonyl)-N,N-dimethylquinoline-4-carboxamide To a stirred mixture of 6-((4-chlorobenzyl)oxy)-2-(4-cyano-4-phenylpiperidine-1-carbonyl)quinoline-4-carboxylic acid (640 mg, 0.535 mmol) and HATU (611 mg, 1.606 mmol) in DCM (8 mL) was added triethylamine (271 mg, 2.68 mmol) and dimethylamine hydrochloride (218 mg, 2.68 mmol). The mixture was stirred at 30° C. for 1 h. Water was added and the mixture was extracted with dichloromethane. The combined organic fractions were washed with brine, dried over Na$_2$SO$_4$, filtered and the solvent was evaporated under reduced pressure, then purified by prep-TLC (DCM: MeOH=20:1) to give 6-((4-chlorobenzyl)oxy)-2-(4-cyano-4-phenylpiperidine-1-carbonyl)-N,N-dimethylquinoline-4-carboxamide. MS (ESI) m/z 553.2 (M+H)

Step C. 2-(4-cyano-4-phenylpiperidine-1-carbonyl)-6-hydroxy-N, N-dimethylquinoline-4-carboxamide To a mixture of 6-((4-chlorobenzyl)oxy)-2-(4-cyano-4-phenylpiperidine-1-carbonyl)-N,N-dimethylquinoline-4-carboxamide (190 mg, 0.344 mmol) in MeOH (5 mL) was added Pd/C (10%, 73.1 mg, 0.069 mmol) under N$_2$ protection. The reaction mixture was stirred at 30° C. under H$_2$ atmosphere with 15 psi for 15 h. The reaction mixture was filtered and the filtrate was concentrated to give 2-(4-cyano-4-phenylpiperidine-1-carbonyl)-6-hydroxy-N,N-dimethylquinoline-4-carboxamide. MS (ESI) m/z 429.2 (M+H)

Step D. 2-(4-cyano-4-phenylpiperidine-1-carbonyl)-N,N-dimethyl-6-((4-methyl-1-oxo-1,3-dihydroisobenzofuran-5-yl)methoxy)quinoline-4-carboxamide To a mixture of 2-(4-cyano-4-phenylpiperidine-1-carbonyl)-6-hydroxy-N,N-dimethylquinoline-4-carboxamide (147 mg, 0.113 mmol) in DMF (5 mL) was added 5-(chloromethyl)-4-methylisobenzofuran-1(3H)-one (26.7 mg, 0.136 mmol) and potassium carbonate (39.1 mg, 0.283 mmol) under N$_2$ protection. Then the reaction mixture was stirred at 25° C. for 5 h. The reaction mixture was filtered and the filtrate was purified by reversed phase HPLC to give 2-(4-cyano-4-phenylpiperidine-1-carbonyl)-N,N-dimethyl-6-((4-methyl-1-oxo-1,3-dihydroisobenzofuran-5-yl)methoxy)quinoline-4-carboxamide.

MS (ESI) m/z 589.2 (M+H)

Example 4 rac-4-chloro-5-(((2-(3-hydroxy-3-methylpyrrolidine-1-carbonyl)-4-(piperidine-1-carbonyl)quinolin-6-yl)oxy)methyl)isobenzofuran-1(3H)-one

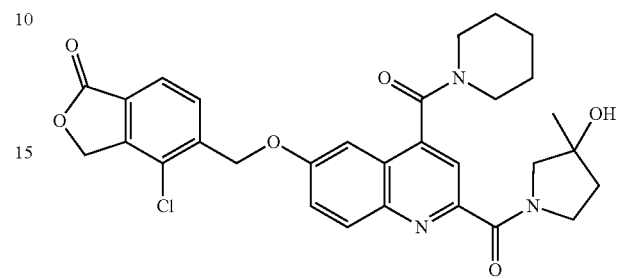

Synthetic Scheme

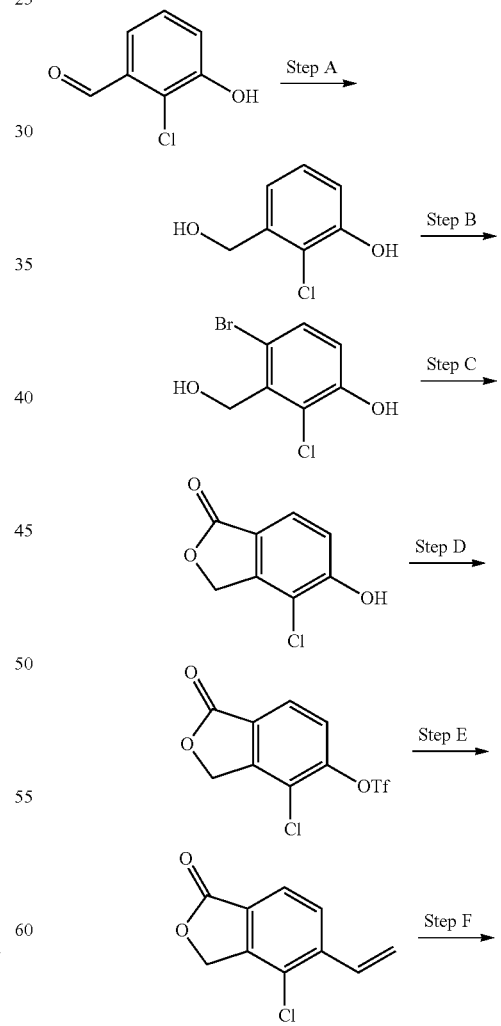

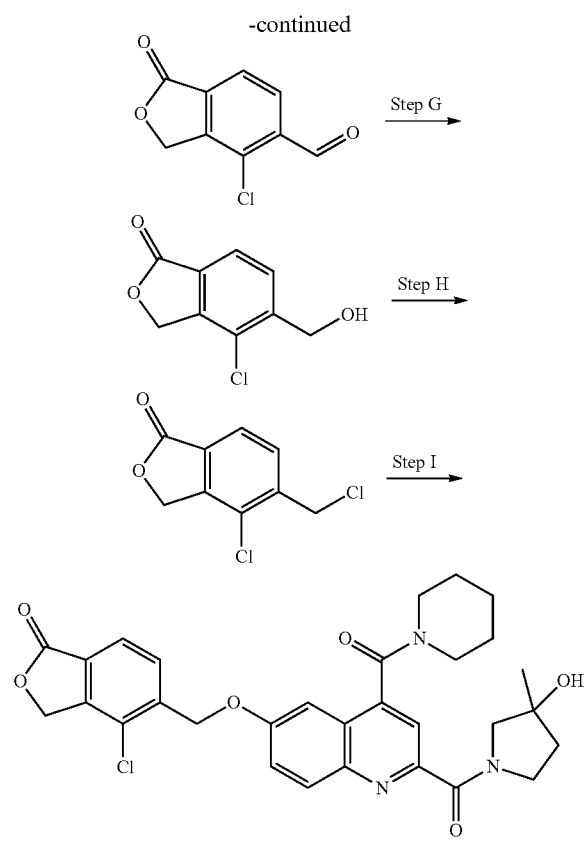

Step A. 2-chloro-3-(hydroxymethyl)phenol

To a mixture of 2-chloro-3-hydroxybenzaldehyde (3.0 g, 19.16 mmol) in MeOH (50 mL) was added NaBH$_4$ (0.725 g, 19.16 mmol) at 0° C. The reaction mixture was stirred at 0° C. for 0.5 h. The reaction was then diluted with EtOAc and water. The aqueous layer was extracted with EtOAc. The combined organic phase was dried over Na$_2$SO$_4$, filtered and concentrated in vacuo to afford 2-chloro-3-(hydroxymethyl)phenol.

Step B. 4-bromo-2-chloro-3-(hydroxymethyl)phenol

To a mixture of 2-chloro-3-(hydroxymethyl)phenol (2.8 g, 17.66 mmol) in TFA (40 mL) was added NBS (3.77 g, 21.19 mmol). The reaction mixture was stirred at 25° C. for 15 h. The reaction mixture was concentrated in vacuo and the residual was re-dissolved in EtOAc and water. The aqueous layer was extracted with EtOAc. The combined organic phase was dried over Na$_2$SO$_4$, filtered and concentrated in vacuo. The crude product was purified by flash column chromatography (eluting with 0-30% EtOAc/Petroleum ether) to give 4-bromo-2-chloro-3-(hydroxymethyl)phenol and recovered 2-chloro-3-(hydroxymethyl)phenol.

Step C. 4-chloro-5-hydroxyisobenzofuran-1(3H)-one

To a mixture of 4-bromo-2-chloro-3-(hydroxymethyl)phenol (3.0 g, 12.63 mmol) in DMF (50 mL) was added copper(I) cyanide (3.39 g, 37.9 mmol). The reaction mixture was stirred at 145° C. for 2 h under N$_2$. Then, water (0.683 g, 37.9 mmol) was added to the above mixture and the resulting mixture was stirred at 100° C. for 18 h. The reaction mixture was cooled to 25° C., diluted with DCM, and filtered through a pad of Celite to remove the solids. The filtrate was concentrated and purified by flash silica gel chromatography (eluted with 20-50% EtOAc/Petroleum ether gradient) to give 4-chloro-5-hydroxyisobenzofuran-1 (3H)-one.

Step D. 4-chloro-1-oxo-1,3-dihydroisobenzofuran-5-yl trifluoromethanesulfonate

To a mixture of 4-chloro-5-hydroxyisobenzofuran-1(3H)-one (2.16 g, 11.70 mmol) and DIPEA (6.13 mL, 35.1 mmol) in DCM (40 mL) was added dropwise Tf$_2$O (3.94 mL, 23.40 mmol) under 0° C. After addition, the reaction mixture was warmed to 25° C. and stirred at 25° C. for 15 h. The reaction mixture was diluted with water. The aqueous layer was extracted with DCM. The combined organic phase was dried over Na$_2$SO$_4$, filtered and concentrated in vacuo. The crude product was purified by flash column chromatography (eluted with 0-30% EtOAc/Petroleum ether gradient) to give 4-chloro-1-oxo-1,3-dihydroisobenzofuran-5-yl trifluoromethanesulfonate.

Step E. 4-chloro-5-vinylisobenzofuran-1 (3H)-one

To a mixture of 4-chloro-1-oxo-1,3-dihydroisobenzofuran-5-yl trifluoromethanesulfonate (2.4 g, 7.58 mmol), potassium vinyltrifluoroborate (2.031 g, 15.16 mmol) and Et$_3$N (2.113 mL, 15.16 mmol) in 2-propanol (40 mL) was added [1,1'-bis(diphenylphosphino)ferrocene]dichloropalladium(II) (0.555 g, 0.758 mmol) under N$_2$. The reaction mixture was stirred at 60° C. for 2 h. The reaction was then diluted with EtOAc and water. The aqueous layer was extracted with EtOAc. The combined organic phase was dried over Na$_2$SO$_4$, filtered and concentrated in vacuo. The crude product was purified by flash silica gel chromatography (eluted with 0-20% EtOAc/Petroleum ether gradient) to give 4-chloro-5-vinylisobenzofuran-1 (3H)-one.

Step F. 4-chloro-1-oxo-1,3-dihydroisobenzofuran-5-carbaldehyde

To a solution of 4-chloro-5-vinylisobenzofuran-1(3H)-one (960 mg, 4.93 mmol) in acetone (30 mL) and water (30 mL) was added potassium osmate (VI) dihydrate (91 mg, 0.247 mmol) and the reaction mixture was stirred for 5 mins. Then, sodium periodate (4220 mg, 19.73 mmol) was added to the reaction. The resulting mixture was stirred at 25° C. for 1 h. The suspension was filtered and the filtrate was concentrated to remove acetone and the aqueous layer was extracted with DCM). The combined organic phase was dried over Na$_2$SO$_4$, filtered and concentrated in vacuo. The crude product was purified by flash column chromatography (eluted with 5-25% EtOAc/Petroleum ether gradient) to give 4-chloro-1-oxo-1,3-dihydroisobenzofuran-5-carbaldehyde.

Step G. 4-chloro-5-(hydroxymethyl)isobenzofuran-1(3H)-one

To a mixture of 4-chloro-1-oxo-1,3-dihydroisobenzofuran-5-carbaldehyde (150 mg, 0.763 mmol) in MeOH (5.0 mL) was added NaBH$_4$ (57.7 mg, 1.526 mmol). The reaction mixture was stirred at 25° C. for 1 h. The reaction was then diluted with EtOAc and water. The aqueous layer was extracted with EtOAc. The combined organic phase was dried over Na₂SO₄, filtered and concentrated in vacuo to afford 4-chloro-5-(hydroxymethyl)isobenzofuran-1(3H)-one. MS (ESI) m/z 198.9 (M+H).

Step H. 4-chloro-5-(chloromethyl)isobenzofuran-1(3H)-one

To a mixture of 4-chloro-5-(hydroxymethyl)isobenzofuran-1(3H)-one (150 mg, 0.755 mmol) in DCM (5.0 mL) was added SOCl₂ (0.20 mL, 2.74 mmol). The reaction mixture was stirred at 25° C. for 2 h. The reaction mixture was diluted with 1N NaHCO₃ until pH=8 and extracted with DCM. The combined organic phase was dried over Na₂SO₄, filtered and concentrated in vacuo to afford 4-chloro-5-(chloromethyl)isobenzofuran-1(3H)-one.

Step I. 4-chloro-5-(((2-(3-hydroxy-3-methylpyrrolidine-1-carbonyl)-4-(piperidine-1-carbonyl)quinolin-6-yl)oxy)methyl)isobenzofuran-1(3H)-one To a mixture of 4-chloro-5-(chloromethyl)isobenzofuran-1(3H)-one (20.38 mg, 0.094 mmol) and K₂CO₃ (32.4 mg, 0.235 mmol) in DMF (2.0 mL) were added (6-hydroxy-2-(3-hydroxy-3-methylpyrrolidine-1-carbonyl)quinolin-4-yl)(piperidin-1-yl)methanone (30 mg, 0.078 mmol) and sodium iodide (11.73 mg, 0.078 mmol). The reaction mixture was stirred at 25° C. for 2 h under N₂. The reaction was purified by reversed phase HPLC to afford 4-chloro-5-(((2-(3-hydroxy-3-methylpyrrolidine-1-carbonyl)-4-(piperidine-1-carbonyl)quinolin-6-yl)oxy)methyl)isobenzofuran-1(3H)-one. MS (ESI) m/z 564.0 (M+H)

Examples 5a & 5b 5-(((2-(3-hydroxy-3-methylpyrrolidine-1-carbonyl)-4-(piperidine-1-carbonyl)quinolin-6-yl)oxy)methyl)-4-methylisobenzofuran-1(3H)-one

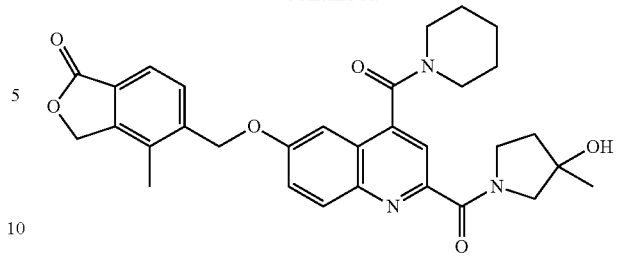

Step A. 5-(((2-(3-hydroxy-3-methylpyrrolidine-1-carbonyl)-4-(piperidine-1-carbonyl) quinolin-6-yl)oxy) methyl)-4-methylisobenzofuran-1(3H)-one To a solution of (6-hydroxy-2-(3-hydroxy-3-methylpyrrolidine-1-carbonyl) quinolin-4-yl) (piperidin-1-yl) methanone (110 mg, 0.287 mmol) and 5-(chloromethyl)-4-methylisobenzofuran-1(3H)-one (67.7 mg, 0.344 mmol) in DMF (3 mL) was added K₂CO₃ (99 mg, 0.717 mmol) under N₂ in a schlenk flask. The reaction mixture was stirred at 30° C. for 16 h. LCMS showed the reaction was complete. The mixture was purified by reverse phase HPLC to give rac-5-(((2-(3-hydroxy-3-methylpyrrolidine-1-carbonyl)-4-(piperidine-1-carbonyl) quinolin-6-yl) oxy) methyl)-4-methylisobenzofuran-1(3H)-one. rac-5-(((2-(3-hydroxy-3-methylpyrrolidine-1-carbonyl)-4-(piperidine-1-carbonyl)quinolin-6-yl)oxy)methyl)-4-methylisobenzofuran-1(3H)-one (80 mg, 0.147 mmol) was separated by SFC (AY, 250 mm×30 mm, 50% 0.1% NH₃·H₂O/EtOH in CO₂) to give faster eluting isomer 5a and slower eluting 5b.

5a: MS (ESI) m/z 544.0 (M+H) 5b: MS (ESI) m/z 544.0 (M+H).

Example 6

(4-(1H-pyrazol-1-yl)piperidin-1-yl)(6-(benzo[d][1,2,3]thiadiazol-6-ylmethoxy)-4-(piperidine-1-carbonyl)quinolin-2-yl)methanone

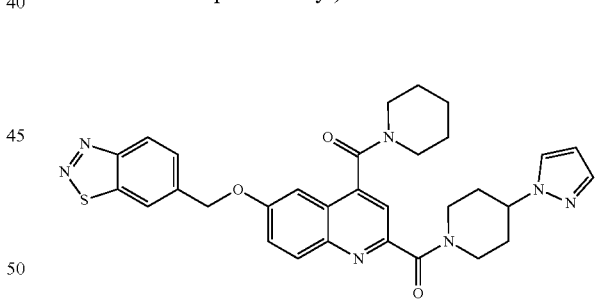

Synthetic Scheme

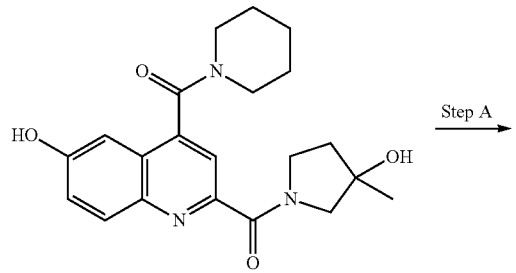

Step A →

Synthetic Scheme

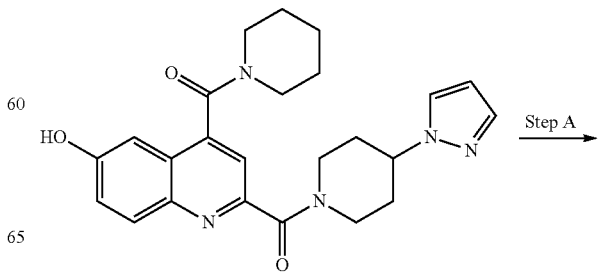

Step A →

-continued

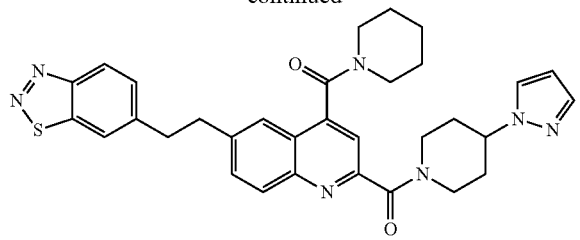

Step A: (4-(1H-pyrazol-1-yl)piperidin-1-yl)(6-(benzo[d][1,2,3]thiadiazol-6-ylmethoxy)-4-(piperidine-1-carbonyl)quinolin-2-yl)methanone To a solution of benzo[d][1,2,3]thiadiazol-6-ylmethanol (20 mg, 0.120 mmol) in 0.5 ml of DCM was added p-toluenesulfonyl chloride (18.35 mg, 0.096 mmol) and triethylamine (14.61 mg, 0.144 mmol), followed by 1 mg of DMAP as catalyst at rt under $N_2$. After stirring for 5 min, a solution of (4-(1H-pyrazol-1-yl)piperidin-1-yl)(6-hydroxy-4-(piperidine-1-carbonyl)quinolin-2-yl)methanone (52.2 mg, 0.120 mmol) in 2 mL of DMF was added to the reaction mixture, followed by addition of $Cs_2CO_3$ (78 mg, 0.24 mmol). The reaction mixture was stirred for 1 h. The reaction mixture was filtered via a syringe filter and the filtrate was purified by reverse phase HPLC to provide (4-(1H-pyrazol-1-yl)piperidin-1-yl)(6-(benzo[d][1,2,3]thiadiazol-6-ylmethoxy)-4-(piperidine-1-carbonyl)quinolin-2-yl)methanone. MS (ES$^+$) m/z: 582.5 (M+H)

Example 7

(4-(1H-pyrazol-1-yl)piperidin-1-yl)(6-(benzo[d][1,2,3]thiadiazol-5-ylmethoxy)-4-(piperidine-1-carbonyl)quinolin-2-yl)methanone

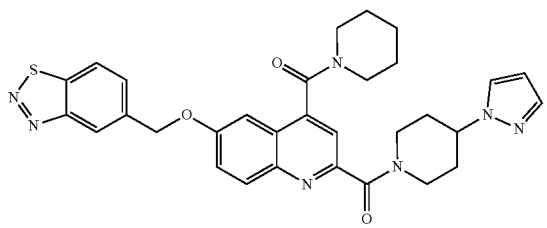 [SMILES: O=C(c1cc(C(=O)N2CCCCC2)c2cc(OCc3ccc4snnc4c3)ccc2n1)N1CCC(n2cccn2)CC1]

Synthetic Scheme

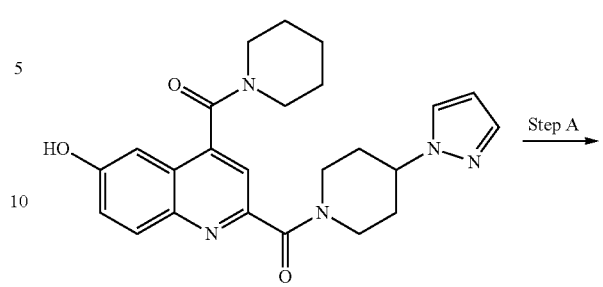

Step A: (4-(1H-pyrazol-1-yl)piperidin-1-yl)(6-(benzo[d][1,2,3]thiadiazol-5-ylmethoxy)-4-(piperidine-1-carbonyl)quinolin-2-yl)methanone To a solution of (4-(1H-pyrazol-1-yl)piperidin-1-yl)(6-hydroxy-4-(piperidine-1-carbonyl)quinolin-2-yl)methanone (180 mg, 0.415 mmol) and 5-(bromomethyl)benzo[d][1,2,3]thiadiazole (95 mg, 0.415 mmol) in DMF (5 ml) was added $Cs_2CO_3$ (271 mg, 0.83 mmol) under $N_2$ at rt. The reaction mixture was stirred at 25 C for 16 h. The reaction mixture was filtered through a syringe filter and the filtrate was purified by reverse phase HPLC to give (4-(1H-pyrazol-1-yl)piperidin-1-yl)(6-(benzo[d][1,2,3]thiadiazol-5-ylmethoxy)-4-(piperidine-1l-carbonyl)quinolin-2-yl)methanone. MS (ESI) m/z 582.5 (M+H)

By using the procedures described above from the appropriately activated benzylic reagent and appropriate starting materials, the following compounds were synthesized and characterized by LC/MS.

| Ex # | Structure | Name | Exact Mass [M + H]$^+$ |
|---|---|---|---|
| 8 | 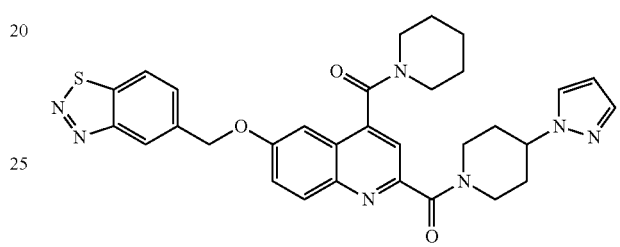 | (4-(1H-pyrazol-1-yl)piperidin-1-yl)(4-(piperidine-1-carbonyl)-6-(3-(pyridin-3-yl)propoxy)quinolin-2-yl)methanone | 553.4 |

| Ex # | Structure | Name | Exact Mass [M + H]+ |
|---|---|---|---|
| 9 | 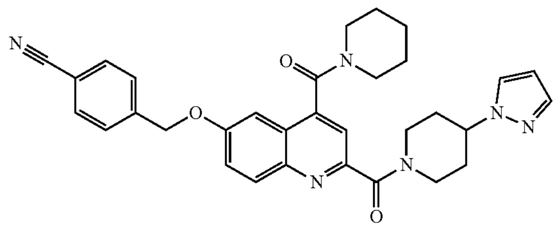 [SMILES: N#Cc1ccc(COc2ccc3nc(C(=O)N4CCC(n5cccn5)CC4)cc(C(=O)N4CCCCC4)c3c2)cc1] | 4-(((2-(4-(1H-pyrazol-1-yl)-piperidine-1-carbonyl)-4-(piperidine-1-carbonyl)-quinolin-6-yl)oxy)methyl)benzonitrile | 549.1 |
| 10 | 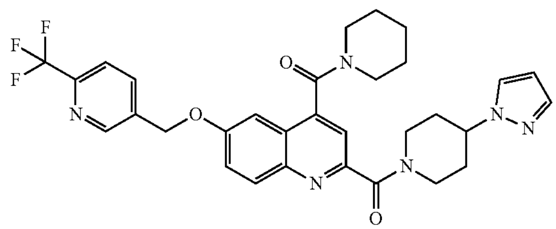 [SMILES: O=C(c1cc(C(=O)N2CCCCC2)c2cc(OCc3ccc(C(F)(F)F)nc3)ccc2n1)N1CCC(n2cccn2)CC1] | (4-(1H-pyrazol-1-yl)piperidin-1-yl)(4-(piperidine-1-carbonyl)-6-((6-(trifluoromethyl)-pyridin-3-yl)methoxy)-quinolin-2-yl)methanone | 593.2 |
| 11 | 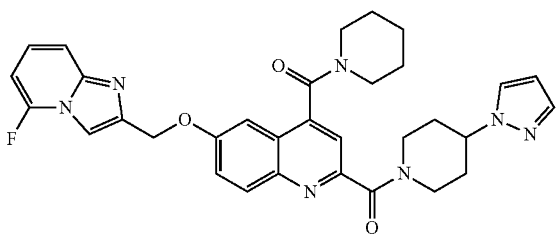 [SMILES: O=C(c1cc(C(=O)N2CCCCC2)c2cc(OCc3cn4c(F)cccc4n3)ccc2n1)N1CCC(n2cccn2)CC1] | (4-(1H-pyrazol-1-yl)piperidin-1-yl)(6-((5-fluoroimidazo[1,2-a]pyridin-2-yl)methoxy)-4-(piperidine-1-carbonyl)-quinolin-2-yl)methanone | 582.3 |
| 12 | 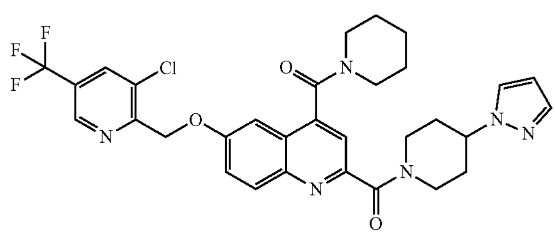 [SMILES: O=C(c1cc(C(=O)N2CCCCC2)c2cc(OCc3ncc(C(F)(F)F)cc3Cl)ccc2n1)N1CCC(n2cccn2)CC1] | (4-(1H-pyrazol-1-yl)piperidin-1-yl)(6-((3-chloro-5-(trifluoromethyl)pyridin-2-yl)methoxy)-4-(piperidine-1-carbonyl)-quinolin-2-yl)methanone | 627.2 |
| 13 | 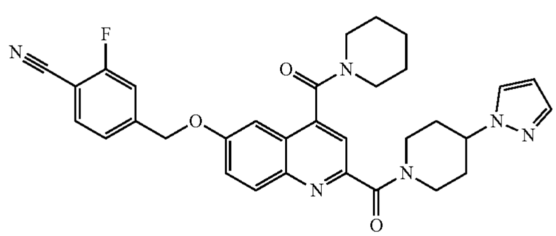 [SMILES: N#Cc1ccc(COc2ccc3nc(C(=O)N4CCC(n5cccn5)CC4)cc(C(=O)N4CCCCC4)c3c2)cc1F] | 4-(((2-(4-(1H-pyrazol-1-yl)-piperidine-1-carbonyl)-4-(piperidine-1-carbonyl)-quinolin-6-yl)oxy)methyl)-2-fluorobenzonitrile | 567.3 |
| 14 | 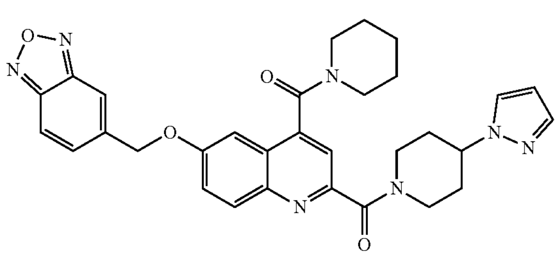 [SMILES: O=C(c1cc(C(=O)N2CCCCC2)c2cc(OCc3ccc4nonc4c3)ccc2n1)N1CCC(n2cccn2)CC1] | (4-(1H-pyrazol-1-yl)piperidin-1-yl)(6-(benzo[c][1,2,5]-oxadiazol-5-ylmethoxy)-4-(piperidine-1-carbonyl)-quinolin-2-yl)methanone | 566.3 |

-continued

| Ex # | Structure | Name | Exact Mass [M + H]+ |
|---|---|---|---|
| 15 | 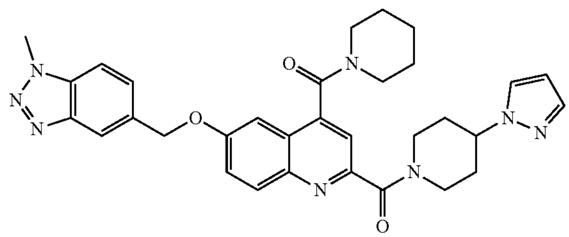 [SMILES: Cn1nnc2cc(COc3ccc4nc(C(=O)N5CCC(n6cccn6)CC5)cc(C(=O)N5CCCCC5)c4c3)ccc21] | (4-(1H-pyrazol-1-yl)piperidin-1-yl)(6-((1-methyl-1H-benzo-[d][1,2,3]triazol-5-yl)methoxy)-4-(piperidine-1-carbonyl)-quinolin-2-yl)methanone | 579.4 |
| 16 | 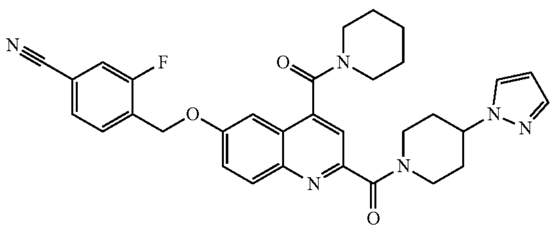 [SMILES: N#Cc1ccc(COc2ccc3nc(C(=O)N4CCC(n5cccn5)CC4)cc(C(=O)N4CCCCC4)c3c2)c(F)c1] | 4-(((2-(4-(1H-pyrazol-1-yl)-piperidine-1-carbonyl)-4-(piperidine-1-carbonyl)-quinolin-6-yl)oxy)methyl)-3-fluorobenzonitrile | 567.3 |
| 17 | 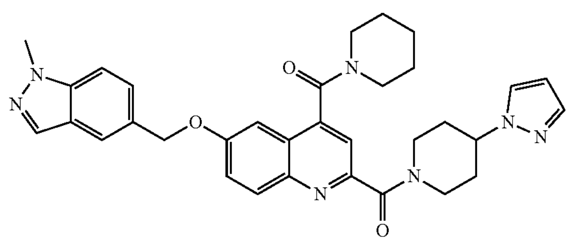 [SMILES: Cn1ncc2cc(COc3ccc4nc(C(=O)N5CCC(n6cccn6)CC5)cc(C(=O)N5CCCCC5)c4c3)ccc21] | (4-(1H-pyrazol-1-yl)piperidin-1-yl)(6-((1-methyl-1H-indazol-5-yl)methoxy)-4-(piperidine-1-carbonyl)quinolin-2-yl)methanone | 578.3 |
| 18 | 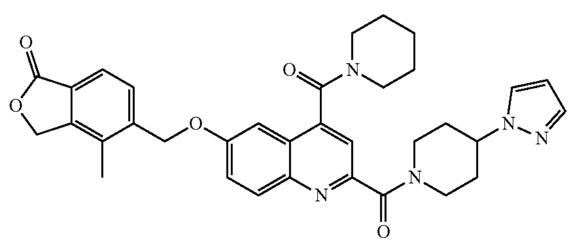 [SMILES: Cc1c(COc2ccc3nc(C(=O)N4CCC(n5cccn5)CC4)cc(C(=O)N4CCCCC4)c3c2)ccc2c1COC2=O] | 5-(((2-(4-(1H-pyrazol-1-yl)-piperidine-1-carbonyl)-4-(piperidine-1-carbonyl)-quinolin-6-yl)oxy)methyl)-4-methylisobenzofuran-1(3H)-one | 594.4 |
| 19 | 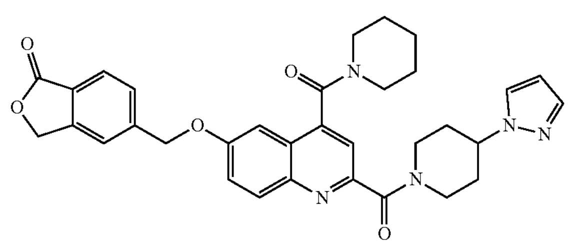 [SMILES: O=C1OCc2cc(COc3ccc4nc(C(=O)N5CCC(n6cccn6)CC5)cc(C(=O)N5CCCCC5)c4c3)ccc21] | 5-(((2-(4-(1H-pyrazol-1-yl)-piperidine-1-carbonyl)-4-(piperidine-1-carbonyl)-quinolin-6-yl)oxy)methyl)-isobenzofuran-1(3H)-one | 580.29 |
| 20 | 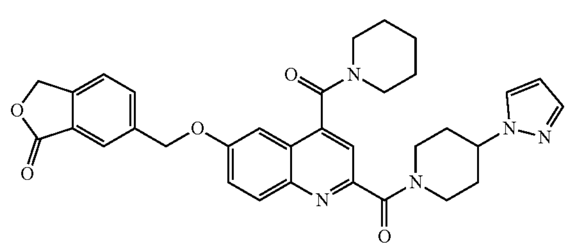 [SMILES: O=C1OCc2ccc(COc3ccc4nc(C(=O)N5CCC(n6cccn6)CC5)cc(C(=O)N5CCCCC5)c4c3)cc21] | 6-(((2-(4-(1H-pyrazol-1-yl)-piperidine-1-carbonyl)-4-(piperidine-1-carbonyl)-quinolin-6-yl)oxy)methyl)-isobenzofuran-1(3H)-one | 580.39 |

-continued

| Ex # | Structure | Name | Exact Mass [M + H]+ |
|---|---|---|---|
| 21 | 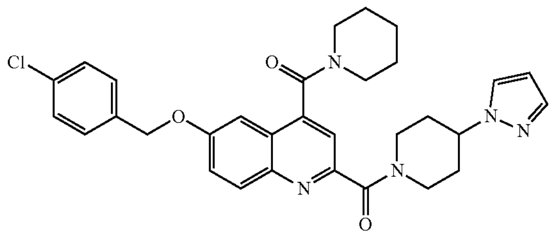 [SMILES: O=C(c1cc(C(=O)N2CCCCC2)c2cc(OCc3ccc(Cl)cc3)ccc2n1)N1CCC(n2cccn2)CC1] | (4-(1H-pyrazol-1-yl)piperidin-1-yl)(6-((4-chlorobenzyl)oxy)-4-(piperidine-1-carbonyl)quinolin-2-yl)methanone | 558.2 |
| 22 | 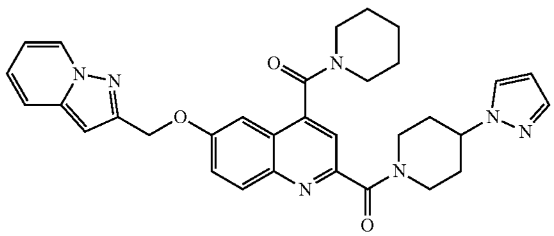 [SMILES: O=C(c1cc(C(=O)N2CCCCC2)c2cc(OCc3cc4ccccn4n3)ccc2n1)N1CCC(n2cccn2)CC1] | (4-(1H-pyrazol-1-yl)piperidin-1-yl)(4-(piperidine-1-carbonyl)-6-(pyrazolo[1,5-a]pyridin-2-ylmethoxy)quinolin-2-yl)methanone | 564.5 |
| 23 | 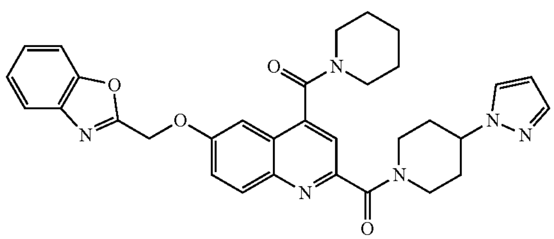 [SMILES: O=C(c1cc(C(=O)N2CCCCC2)c2cc(OCc3nc4ccccc4o3)ccc2n1)N1CCC(n2cccn2)CC1] | (4-(1H-pyrazol-1-yl)piperidin-1-yl)(6-(benzo[d]oxazol-2-ylmethoxy)-4-(piperidine-1-carbonyl)quinolin-2-yl)methanone | 565.5 |
| 24 | 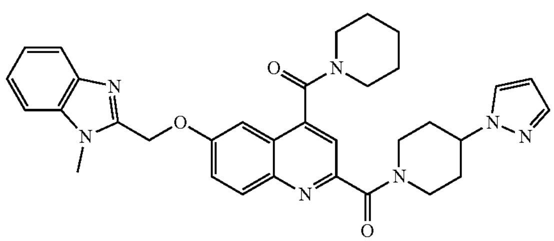 [SMILES: Cn1c(COc2ccc3nc(C(=O)N4CCC(n5cccn5)CC4)cc(C(=O)N4CCCCC4)c3c2)nc2ccccc21] | (4-(1H-pyrazol-1-yl)piperidin-1-yl)(6-((1-methyl-1H-benzo[d]imidazol-2-yl)methoxy)-4-(piperidine-1-carbonyl)quinolin-2-yl)methanone | 578.6 |
| 25 | 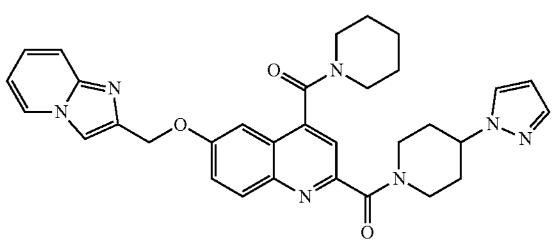 [SMILES: O=C(c1cc(C(=O)N2CCCCC2)c2cc(OCc3cn4ccccc4n3)ccc2n1)N1CCC(n2cccn2)CC1] | (4-(1H-pyrazol-1-yl)piperidin-1-yl)(6-(imidazo[1,2-a]pyridin-2-ylmethoxy)-4-(piperidine-1-carbonyl)quinolin-2-yl)methanone | 564.6 |
| 26 | 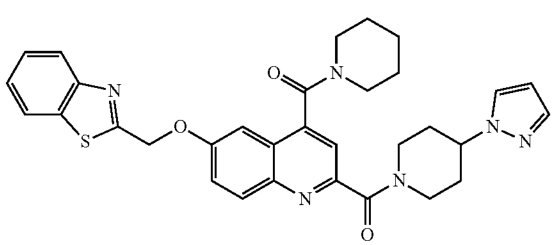 [SMILES: O=C(c1cc(C(=O)N2CCCCC2)c2cc(OCc3nc4ccccc4s3)ccc2n1)N1CCC(n2cccn2)CC1] | (4-(1H-pyrazol-1-yl)piperidin-1-yl)(6-(benzo[d]thiazol-2-ylmethoxy)-4-(piperidine-1-carbonyl)quinolin-2-yl)methanone | 581.5 |

Example 27

1-(6-((4-chloro-2-cyanobenzyl)oxy)-4-(piperidine-1l-carbonyl)quinoline-2-carbonyl)-4-phenylpiperidine-4-carbonitrile

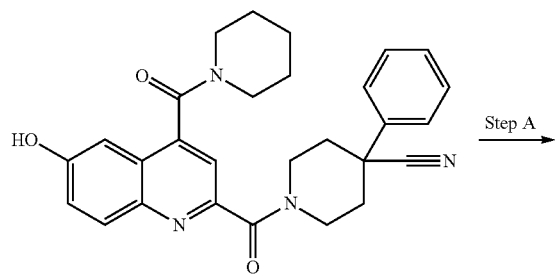

Step A

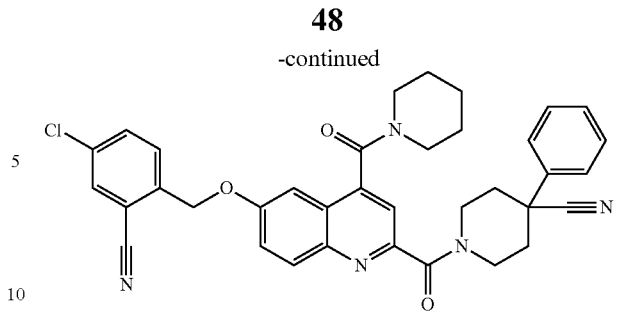

To a stirred solution of 1-(6-hydroxy-4-(piperidine-1l-carbonyl)quinoline-2-carbonyl)-4-phenylpiperidine-4-carbonitrile (20 mg, 0.043 mmol) and $K_2CO_3$ (11.80 mg, 0.085 mmol) in DMF (1.5 ml) was added 2-(bromomethyl)-5-chlorobenzonitrile (11.81 mg, 0.051 mmol). The reaction mixture was stirred at 20° C. for 4 h. The reaction mixture was filtered and purified by reverse phase HPLC to provide 1-(6-((4-chloro-2-cyanobenzyl)oxy)-4-(piperidine-1l-carbonyl)quinoline-2-carbonyl)-4-phenylpiperidine-4-carbonitrile. MS (ESI) m/z 618.2 (M+H).

By using the procedures described above from the appropriately activated benzylic reagent and appropriate starting materials, the following compounds were synthesized and characterized by LC/MS.

| Ex # | Structure | Name | Exact Mass [M + H]+ |
|---|---|---|---|
| 28 | 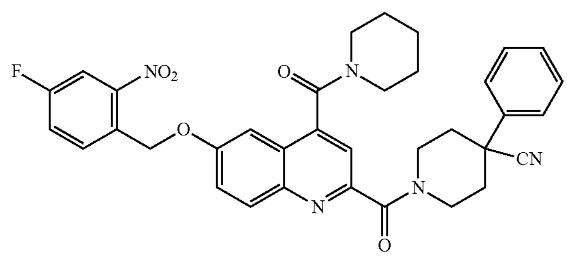 [SMILES: N#CC1(c2ccccc2)CCN(C(=O)c2cc(C(=O)N3CCCCC3)c3cc(OCc4ccc(F)cc4[N+](=O)[O-])ccc3n2)CC1] | 1-(6-((4-fluoro-2-nitrobenzyl)oxy)-4-(piperidine-1-carbonyl)quinoline-2-carbonyl)-4-phenylpiperidine-4-carbonitrile | 622.4 |
| 29 | 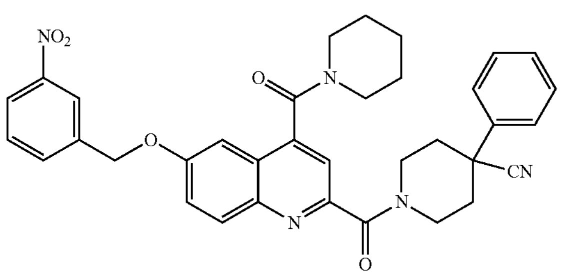 [SMILES: N#CC1(c2ccccc2)CCN(C(=O)c2cc(C(=O)N3CCCCC3)c3cc(OCc4cccc([N+](=O)[O-])c4)ccc3n2)CC1] | 1-(6-((3-nitrobenzyl)oxy)-4-(piperidine-1-carbonyl)quinoline-2-carbonyl)-4-phenylpiperidine-4-carbonitrile | 604.4 |
| 30 | 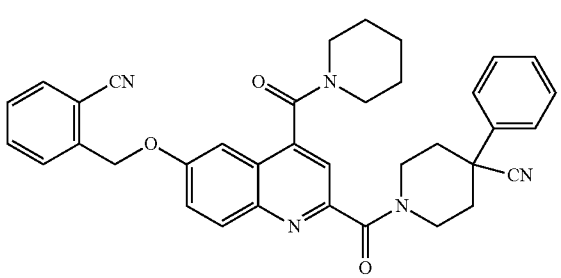 [SMILES: N#Cc1ccccc1COc1ccc2nc(C(=O)N3CCC(C#N)(c4ccccc4)CC3)cc(C(=O)N3CCCCC3)c2c1] | 1-(6-((2-cyanobenzyl)oxy)-4-(piperidine-1-carbonyl)quinoline-2-carbonyl)-4-phenylpiperidine-4-carbonitrile | 584.4 |

| Ex # | Structure | Name | Exact Mass [M + H]+ |
|---|---|---|---|
| 31 | 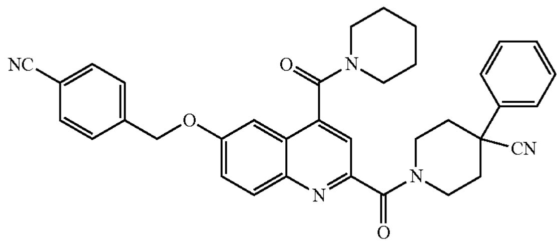 [SMILES: N#Cc1ccc(COc2ccc3nc(C(=O)N4CCC(C#N)(c5ccccc5)CC4)cc(C(=O)N4CCCCC4)c3c2)cc1] | 1-(6-((4-cyanobenzyl)oxy)-4-(piperidine-1-carbonyl)quinoline-2-carbonyl)-4-phenyl-piperidine-4-carbonitrile | 584.4 |
| 32 | 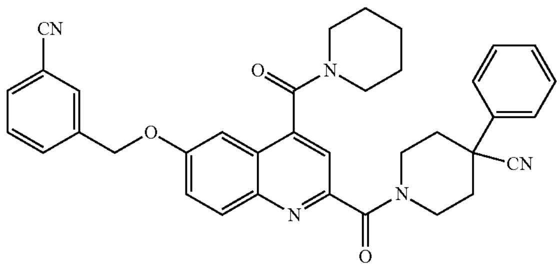 | 1-(6-((3-cyanobenzyl)oxy)-4-(piperidine-1-carbonyl)quinoline-2-carbonyl)-4-phenyl-piperidine-4-carbonitrile | 584.3 |
| 33 | 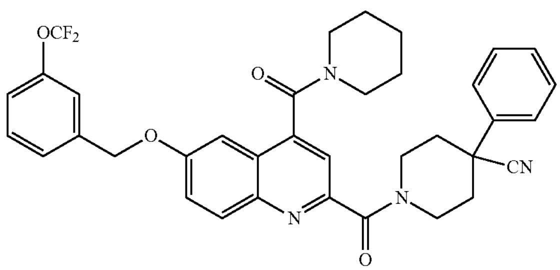 | 1-(6-((3-(difluoro-l3-methoxy)phenyl)methoxy)-4-(piperidine-1-carbonyl)quinoline-2-carbonyl)-4-phenyl-piperidine-4-carbonitrile | 625.4 |
| 34 | 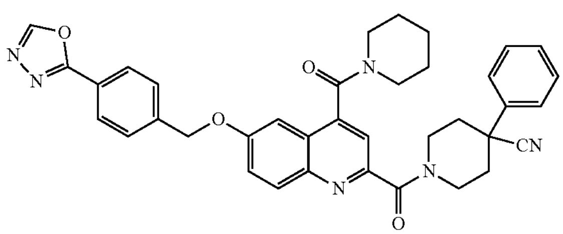 [SMILES: N#CC1(c2ccccc2)CCN(C(=O)c2cc(C(=O)N3CCCCC3)c3cc(OCc4ccc(-c5nnco5)cc4)ccc3n2)CC1] | 1-(6-((4-(1,3,4-oxadiazol-2-yl)benzyl)oxy)-4-(piperidine-1-carbonyl)quinoline-2-carbonyl)-4-phenylpiperidine-4-carbonitrile | 627.4 |
| 35 | 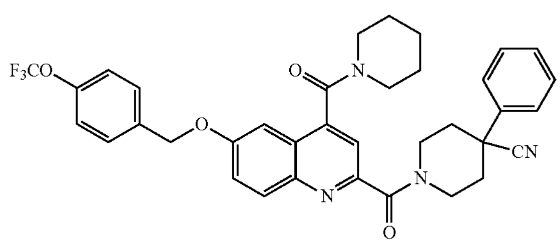 [SMILES: N#CC1(c2ccccc2)CCN(C(=O)c2cc(C(=O)N3CCCCC3)c3cc(OCc4ccc(OC(F)(F)F)cc4)ccc3n2)CC1] | 4-phenyl-1-(4-(piperidine-1-carbonyl)-6-((4-(trifluoromethoxy)benzyl)oxy)quinoline-2-carbonyl)piperidine-4-carbonitrile | 643.4 |
| 36 | 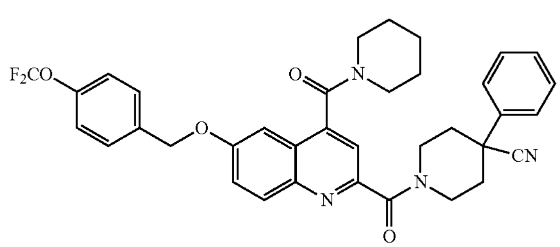 | 1-(6-((4-(difluoro-l3-methoxy)phenyl)methoxy)-4-(piperidine-1-carbonyl)quinoline-2-carbonyl)-4-phenyl-piperidine-4-carbonitrile | 625.4 |

| Ex # | Structure | Name | Exact Mass [M + H]+ |
|---|---|---|---|
| 37 | 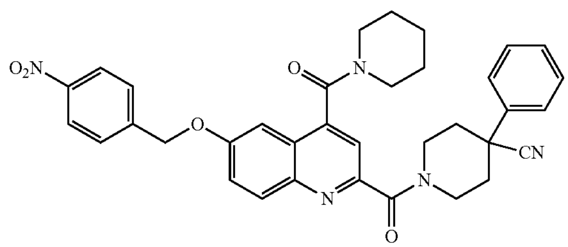 [SMILES: N#CC1(c2ccccc2)CCN(C(=O)c2cc(C(=O)N3CCCCC3)c3cc(OCc4ccc([N+](=O)[O-])cc4)ccc3n2)CC1] | 1-(6-((4-nitrobenzyl)oxy)-4-(piperidine-1-carbonyl)quinoline-2-carbonyl)-4-phenyl-piperidine-4-carbonitrile | 604.3 |
| 38 | 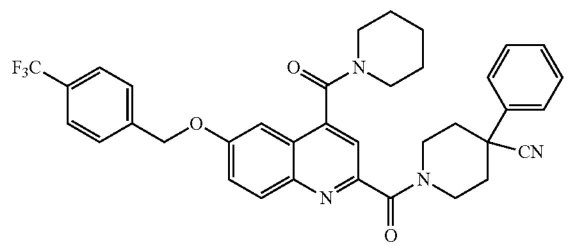 [SMILES: N#CC1(c2ccccc2)CCN(C(=O)c2cc(C(=O)N3CCCCC3)c3cc(OCc4ccc(C(F)(F)F)cc4)ccc3n2)CC1] | 4-phenyl-1-(4-(piperidine-1-carbonyl)-6-((4-(trifluoromethyl)benzyl)oxy)quinoline-2-carbonyl)piperidine-4-carbonitrile | 627.4 |
| 39 | 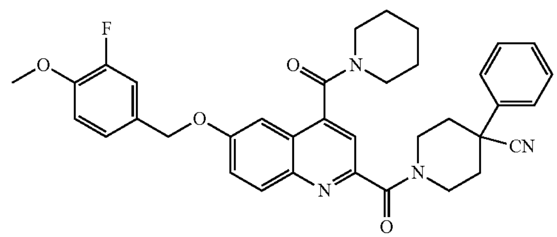 [SMILES: COc1ccc(COc2ccc3nc(C(=O)N4CCC(C#N)(c5ccccc5)CC4)cc(C(=O)N4CCCCC4)c3c2)cc1F] | 1-(6-((3-fluoro-4-methoxybenzyl)oxy)-4-(piperidine-1-carbonyl)quinoline-2-carbonyl)-4-phenylpiperidine-4-carbonitrile | 607.4 |
| 40 | 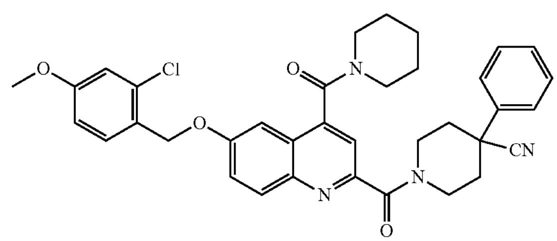 [SMILES: COc1ccc(COc2ccc3nc(C(=O)N4CCC(C#N)(c5ccccc5)CC4)cc(C(=O)N4CCCCC4)c3c2)c(Cl)c1] | 1-(6-((2-chloro-4-methoxybenzyl)oxy)-4-(piperidine-1-carbonyl)quinoline-2-carbonyl)-4-phenylpiperidine-4-carbonitrile | 623.4 |
| 41 | 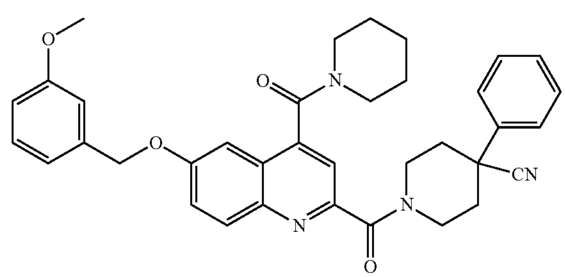 [SMILES: COc1cccc(COc2ccc3nc(C(=O)N4CCC(C#N)(c5ccccc5)CC4)cc(C(=O)N4CCCCC4)c3c2)c1] | 1-(6-((3-methoxybenzyl)oxy)-4-(piperidine-1-carbonyl)quinoline-2-carbonyl)-4-phenyl-piperidine-4-carbonitrile | 589.4 |
| 42 | 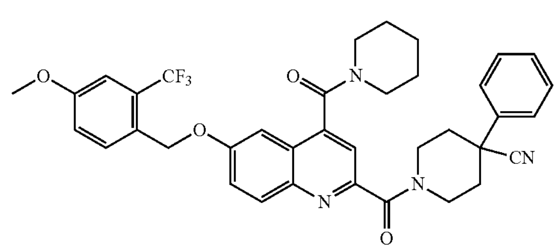 [SMILES: COc1ccc(COc2ccc3nc(C(=O)N4CCC(C#N)(c5ccccc5)CC4)cc(C(=O)N4CCCCC4)c3c2)c(C(F)(F)F)c1] | 1-(6-((4-methoxy-2-(trifluoromethyl)benzyl)oxy)-4-(piperidine-1-carbonyl)quinoline-2-carbonyl)-4-phenyl-piperidine-4-carbonitrile | 657.5 |

-continued

| Ex # | Structure | Name | Exact Mass [M + H]+ |
|---|---|---|---|
| 43 | 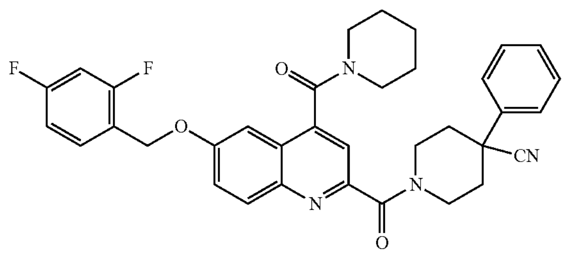 [SMILES: N#CC1(c2ccccc2)CCN(C(=O)c2cc(C(=O)N3CCCCC3)c3cc(OCc4ccc(F)cc4F)ccc3n2)CC1] | 1-(6-((2,4-difluorobenzyl)-oxy)-4-(piperidine-1-carbonyl)quinoline-2-carbonyl)-4-phenylpiperidine-4-carbonitrile | 595.3 |
| 44 | 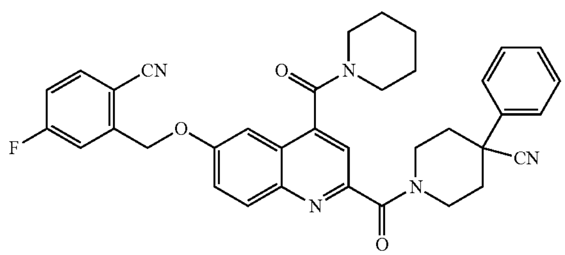 [SMILES: N#Cc1ccc(F)cc1COc1ccc2nc(C(=O)N3CCC(C#N)(c4ccccc4)CC3)cc(C(=O)N3CCCCC3)c2c1] | 1-(6-((2-cyano-5-fluoro-benzyl)oxy)-4-(piperidine-1-carbonyl)quinoline-2-carbonyl)-4-phenylpiperidine-4-carbonitrile | 602.3 |
| 45 | 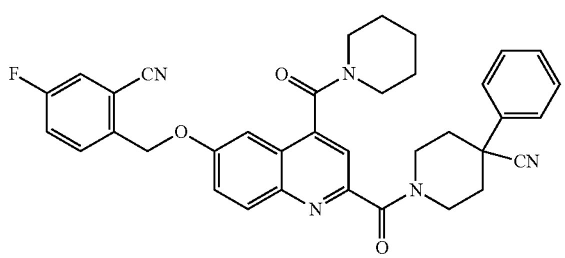 [SMILES: N#Cc1cc(F)ccc1COc1ccc2nc(C(=O)N3CCC(C#N)(c4ccccc4)CC3)cc(C(=O)N3CCCCC3)c2c1] | 1-(6-((2-cyano-4-fluoro-benzyl)oxy)-4-(piperidine-1-carbonyl)quinoline-2-carbonyl)-4-phenylpiperidine-4-carbonitrile | 602.3 |
| 46 | 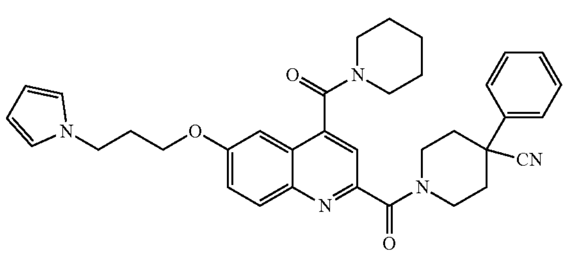 [SMILES: N#CC1(c2ccccc2)CCN(C(=O)c2cc(C(=O)N3CCCCC3)c3cc(OCCCn4cccc4)ccc3n2)CC1] | 1-(6-(3-(1H-pyrrol-1-yl)-propoxy)-4-(piperidine-1-carbonyl)quinoline-2-carbonyl)-4-phenylpiperidine-4-carbonitrile | 576.4 |
| 47 | 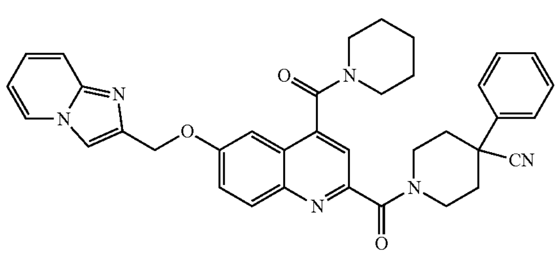 [SMILES: N#CC1(c2ccccc2)CCN(C(=O)c2cc(C(=O)N3CCCCC3)c3cc(OCc4cn5ccccc5n4)ccc3n2)CC1] | 1-(6-(imidazo[1,2-a]pyridin-2-ylmethoxy)-4-(piperidine-1-carbonyl)quinoline-2-carbonyl)-4-phenylpiperidine-4-carbonitrile | 599.4 |

| Ex # | Structure | Name | Exact Mass [M + H]+ |
|---|---|---|---|
| 48 | 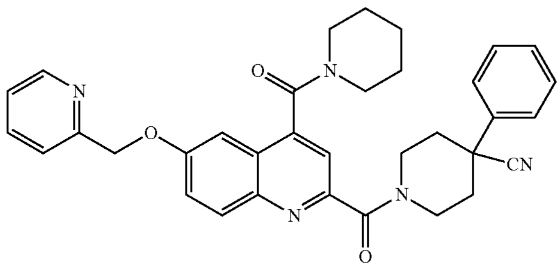 [SMILES: N#CC1(c2ccccc2)CCN(C(=O)c2cc(C(=O)N3CCCCC3)c3cc(OCc4ccccn4)ccc3n2)CC1] | 4-phenyl-1-(4-(piperidine-1-carbonyl)-6-(pyridin-2-yl-methoxy)quinoline-2-carbonyl)piperidine-4-carbonitrile | 560.3 |
| 49 | 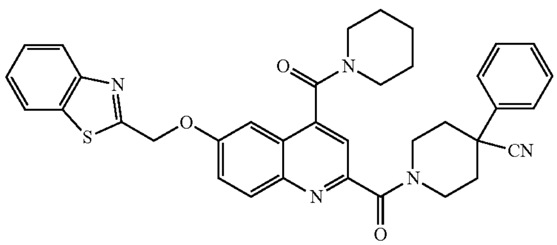 | 1-(6-(benzo[d]thiazol-2-yl-methoxy)-4-(piperidine-1-carbonyl)quinoline-2-carbonyl)-4-phenylpiperidine-4-carbonitrile | 616.4 |
| 50 | 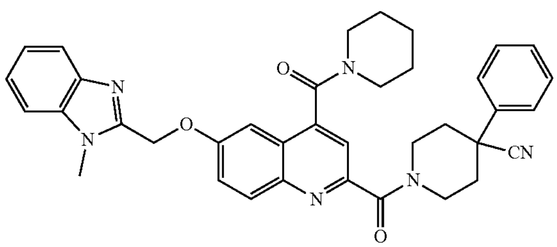 [SMILES: Cn1c(COc2ccc3nc(C(=O)N4CCC(C#N)(c5ccccc5)CC4)cc(C(=O)N4CCCCC4)c3c2)nc2ccccc21] | 1-(6-((1-methyl-1H-benzo[d]-imidazol-2-yl)methoxy)-4-(piperidine-1-carbonyl)quinoline-2-carbonyl)-4-phenyl-piperidine-4-carbonitrile | 613.3 |
| 51 | 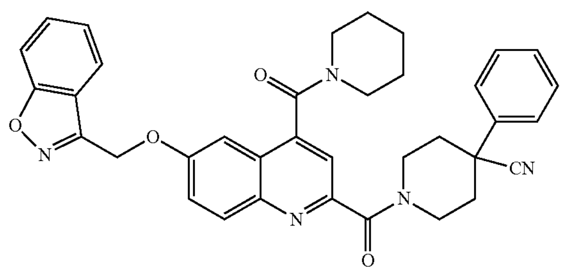 [SMILES: N#CC1(c2ccccc2)CCN(C(=O)c2cc(C(=O)N3CCCCC3)c3cc(OCc4noc5ccccc45)ccc3n2)CC1] | 1-(6-(benzo[d]isoxazol-3-yl-methoxy)-4-(piperidine-1-carbonyl)quinoline-2-carbonyl)-4-phenylpiperidine-4-carbonitrile | 600.3 |

Example 52

(4-(1H-pyrazol-1-yl)piperidin-1-yl)(6-(benzo[d]thi-azol-2-ylmethoxy)-4-(4-fluoropiperidine-1-carbonyl)quinolin-2-yl)methanone

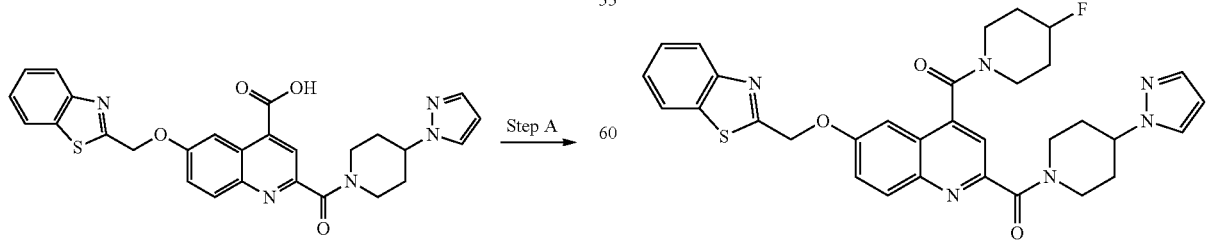

To a mixture of 2-(4-(1H-pyrazol-1-yl)piperidine-1-carbonyl)-6-(benzo[d]thiazol-2-ylmethoxy)quinoline-4-carboxylic acid (32 mg, 0.062 mmol), 4-fluoropiperidine (7.71 mg, 0.075 mmol) and TEA (0.026 ml, 0.187 mmol) in DMF (1.5 ml) was added HATU (28.4 mg, 0.075 mmol). The reaction mixture was stirred at 25° C. for 2 h. The reaction mixture was purified by reverse phase HPLC to afford (4-(1H-pyrazol-1-yl)piperidin-1-yl)(6-(benzo[d]thiazol-2-ylmethoxy)-4-(4-fluoropiperidine-1-carbonyl)quinolin-2-yl)methanone. MS (ESI) m z 599.2 (M+H).

By using the procedure described above and from appropriate starting materials, the following compounds were synthesized and characterized by LC/MS.

| Ex # | Structure | Name | Exact Mass [M + H]+ |
|---|---|---|---|
| 53 | 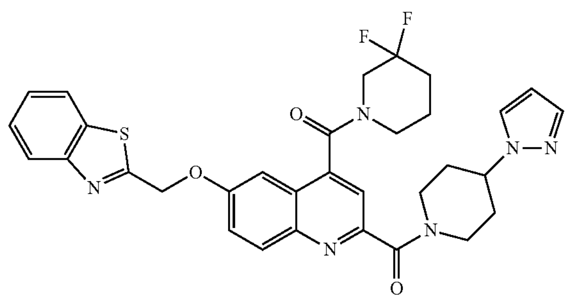 [SMILES: O=C(c1cc(C(=O)N2CCCC(F)(F)C2)c2cc(OCc3nc4ccccc4s3)ccc2n1)N1CCC(n2cccn2)CC1] | (4-(1H-pyrazol-1-yl)piperidin-1-yl)(6-(benzo[d]thiazol-2-ylmethoxy)-4-(3,3-difluoro-piperidine-1-carbonyl)quinolin-2-yl)methanone | 617.2 |
| 54 | 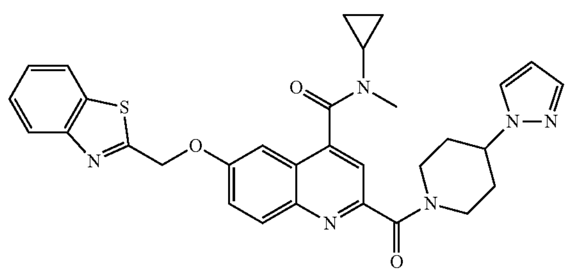 [SMILES: CN(C(=O)c1cc(C(=O)N2CCC(n3cccn3)CC2)nc2ccc(OCc3nc4ccccc4s3)cc12)C1CC1] | 2-(4-(1H-pyrazol-1-yl)piperidine-1-carbonyl)-6-(benzo[d]thiazol-2-ylmethoxy)-N-cyclopropyl-N-methylquinoline-4-carboxamide | 567.0 |
| 55 | 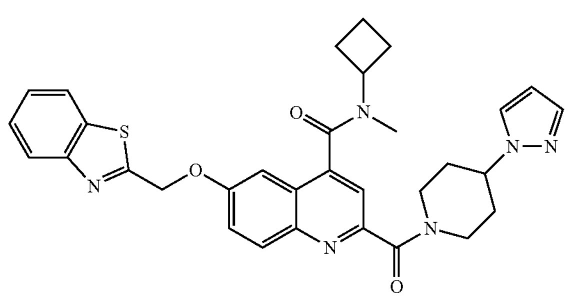 [SMILES: CN(C(=O)c1cc(C(=O)N2CCC(n3cccn3)CC2)nc2ccc(OCc3nc4ccccc4s3)cc12)C1CCC1] | 2-(4-(1H-pyrazol-1-yl)piperidine-1-carbonyl)-6-(benzo[d]thiazol-2-ylmethoxy)-N-cyclobutyl-N-methylquinoline-4-carboxamide | 581.0 |

Example 56

(4-(1H-imidazol-1-yl)piperidin-1-yl)(6-(benzodithiazol-2-ylmethoxy)-4-(piperidine-1-carbonyl)quinolin-2-yl)methanone

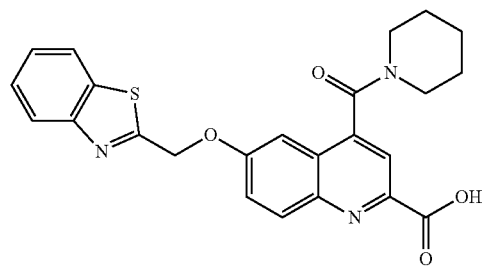

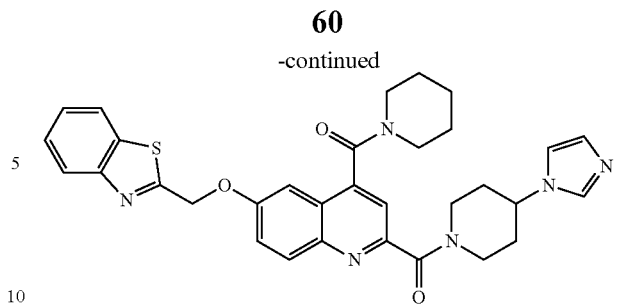

A mixture of 6-(benzo[d]thiazol-2-ylmethoxy)-4-(piperidine-1-carbonyl)quinoline-2-carboxylic acid (41.4 mg, 0.093 mmol), 4-(1H-imidazol-1-yl)piperidine (20 mg, 0.132 mmol), EDC (50.7 mg, 0.265 mmol), and pyridine (0.5 mL, 6.18 mmol) was stirred at 25° C. for 16 h. The residue was purified by reverse phase HPLC to provide (4-(1H-imidazol-1-yl)piperidin-1-yl)(6-(benzo[d]thiazol-2-ylmethoxy)-4-(piperidine-1-carbonyl)quinolin-2-yl)methanone. MS (ESI) m/z 581.2 (M+H)

By using the procedure described above and from appropriate starting materials, the following compounds were synthesized and characterized by LC/MS.

| Ex # | Structure | Name | Exact Mass [M + H]+ |
|---|---|---|---|
| 57 | 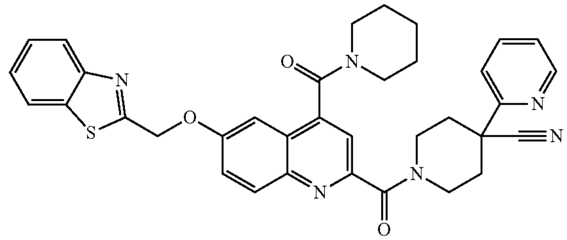 [SMILES: N#CC1(c2ccccn2)CCN(C(=O)c2cc(C(=O)N3CCCCC3)c3cc(OCc4nc5ccccc5s4)ccc3n2)CC1] | 1-(6-(benzo[d]thiazol-2-ylmethoxy)-4-(piperidine-1-carbonyl)quinoline-2-carbonyl)-4-(pyridin-2-yl)-piperidine-4-carbonitrile | 617.0 |
| 58 | 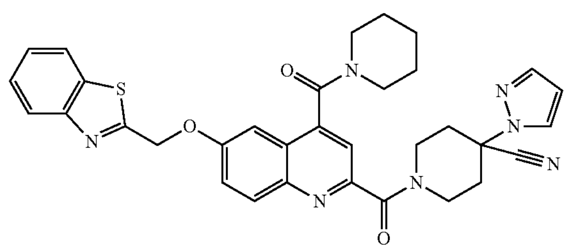 [SMILES: N#CC1(n2cccn2)CCN(C(=O)c2cc(C(=O)N3CCCCC3)c3cc(OCc4nc5ccccc5s4)ccc3n2)CC1] | 1-(6-(benzo[d]thiazol-2-ylmethoxy)-4-(piperidine-1-carbonyl)quinoline-2-carbonyl)-4-(1H-pyrazol-1-yl)piperidine-4-carbonitrile | 606.0 |
| 59 | 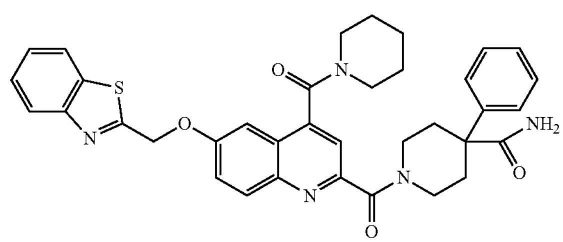 [SMILES: NC(=O)C1(c2ccccc2)CCN(C(=O)c2cc(C(=O)N3CCCCC3)c3cc(OCc4nc5ccccc5s4)ccc3n2)CC1] | 1-(6-(benzo[d]thiazol-2-ylmethoxy)-4-(piperidine-1-carbonyl)quinoline-2-carbonyl)-4-phenylpiperidine-4-carboxamide | 634.3 |
| 60 | 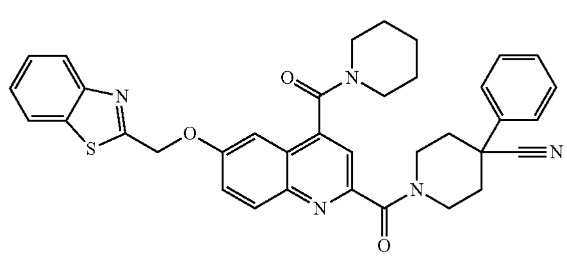 | 1-(6-(benzo[d]thiazol-2-ylmethoxy)-4-(piperidine-1-carbonyl)quinoline-2-carbonyl)-4-phenylpiperidine-4-carbonitrile | 616.3 |

| Ex # | Structure | Name | Exact Mass [M + H]+ |
|---|---|---|---|
| 61 | 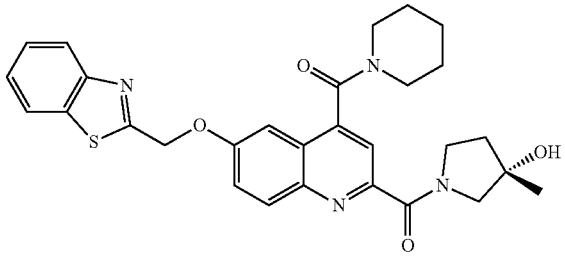 [SMILES: C[C@]1(O)CCN(C(=O)c2cc(C(=O)N3CCCCC3)c3cc(OCc4nc5ccccc5s4)ccc3n2)C1] | (S)(6-(benzo[d]thiazol-2-ylmethoxy)-2-(3-hydroxy-3-methylpyrrolidine-1-carbonyl)quinolin-4-yl)-(piperidin-1-yl)methanone | 531.0 |
| 62 | 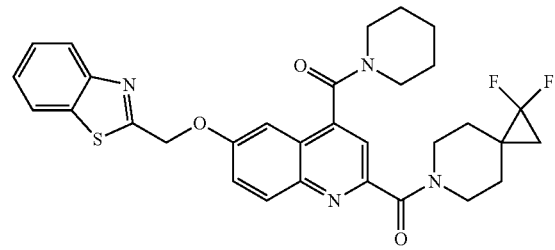 [SMILES: O=C(c1cc(C(=O)N2CCCCC2)c2cc(OCc3nc4ccccc4s3)ccc2n1)N1CCC2(CC1)CC2(F)F] | (6-(benzo[d]thiazol-2-yl-methoxy)-2-(1,1-difluoro-6-azaspiro[2.5]octane-6-carbonyl)quinolin-4-yl)-(piperidin-1-yl)methanone | 577.1 |
| 63 | 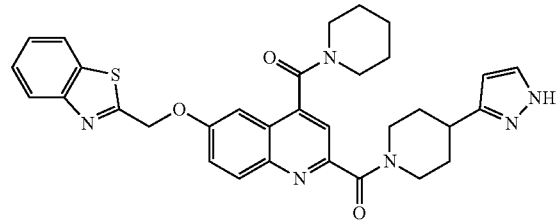 [SMILES: O=C(c1cc(C(=O)N2CCCCC2)c2cc(OCc3nc4ccccc4s3)ccc2n1)N1CCC(c2cc[nH]n2)CC1] | (4-(1H-pyrazol-3-yl)piperi-din-1-yl)(6-(benzo[d]-thiazol-2-ylmethoxy)-4-(piperidine-1-carbonyl)-quinolin-2-yl)methanone | 581.5 |
| 64 | 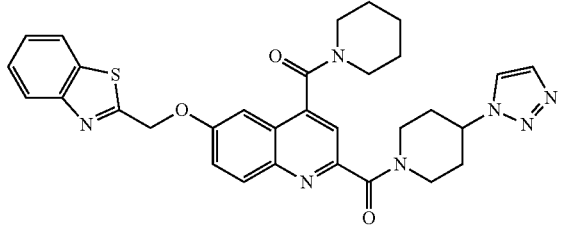 [SMILES: O=C(c1cc(C(=O)N2CCCCC2)c2cc(OCc3nc4ccccc4s3)ccc2n1)N1CCC(n2ccnn2)CC1] | (4-(1H-1,2,3-triazol-1-yl)-piperidin-1-yl)(6-(benzo-[d]thiazol-2-ylmethoxy)-4-(piperidine-1-carbonyl)-quinolin-2-yl)methanone | 582.5 |
| 65 | 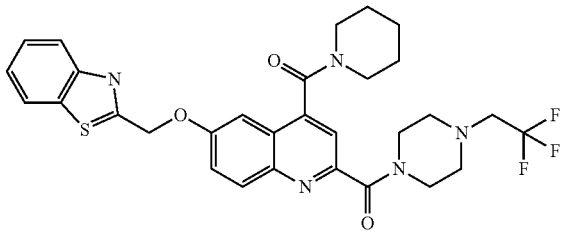 | (6-(benzo[d]thiazol-2-yl-methoxy)-2-(4-(2,2,2-trifluoroethyl)piperazine-1-carbonyl)quinolin-4-yl)-(piperidin-1-yl)methanone | 598.2 |
| 66 | 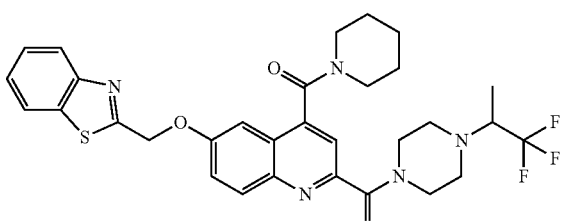 | (6-(benzo[d]thiazol-2-yl-methoxy)-2-(4-(1,1,1-trifluoropropan-2-yl)-piperazine-1-carbonyl)-quinolin-4-yl)(piperidin-1-yl)methanone | 612.3 |

-continued

| Ex # | Structure | Name | Exact Mass [M + H]+ |
|---|---|---|---|
| 67 | 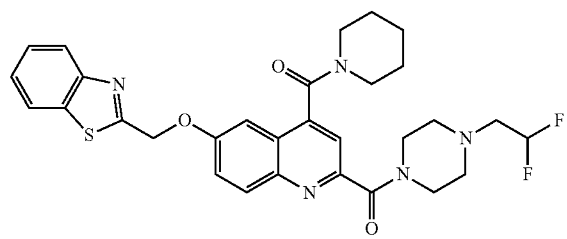 [SMILES: O=C(c1cc(C(=O)N2CCCCC2)c2cc(OCc3nc4ccccc4s3)ccc2n1)N1CCN(CC(F)F)CC1] | (6-(benzo[d]thiazol-2-yl-methoxy)-2-(4-(2,2-difluoroethyl)piperazine-1-carbonyl)quinolin-4-yl)-(piperidin-1-yl)methanone | 580.3 |
| 68 | 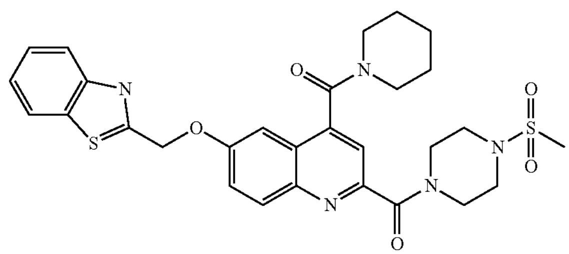 | (6-(benzo[d]thiazol-2-yl-methoxy)-2-(4-(methyl-sulfonyl)piperazine-1-carbonyl)quinolin-4-yl)-(piperidin-1-yl)methanone | 594.3 |
| 69 | 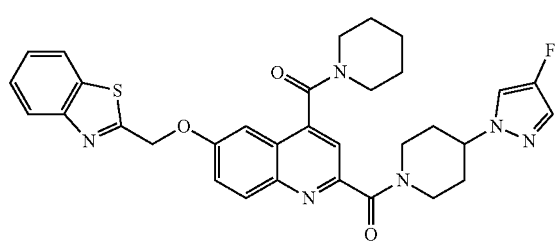 [SMILES: O=C(c1cc(C(=O)N2CCCCC2)c2cc(OCc3nc4ccccc4s3)ccc2n1)N1CCC(n2cc(F)cn2)CC1] | (6-(benzo[d]thiazol-2-yl-methoxy)-2-(4-(4-fluoro-1H-pyrazol-1-yl)piperidine-1-carbonyl)quinolin-4-yl)(piperidin-1-yl)methanone | 599.2 |
| 70 | 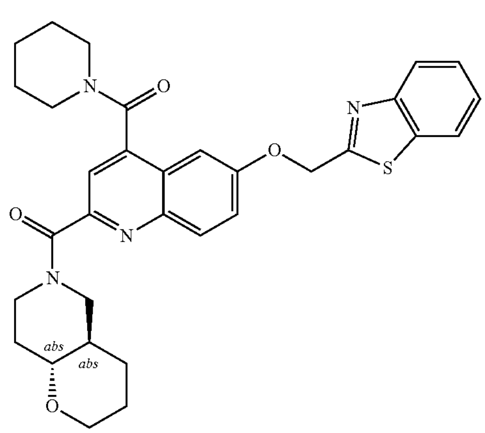 [SMILES: O=C(c1cc(C(=O)N2CCCCC2)c2cc(OCc3nc4ccccc4s3)ccc2n1)N1CC[C@H]2OCCC[C@@H]2C1] | (6-(benzo[d]thiazol-2-yl-methoxy)-2-((4aR,8aR-octahydro-2H-pyrano[3,2-c]pyridine-6-carbonyl)-quinolin-4-yl)(piperidin-1-yl)methanone | 571.3 |

| Ex # | Structure | Name | Exact Mass [M + H]+ |
|---|---|---|---|
| 71 | 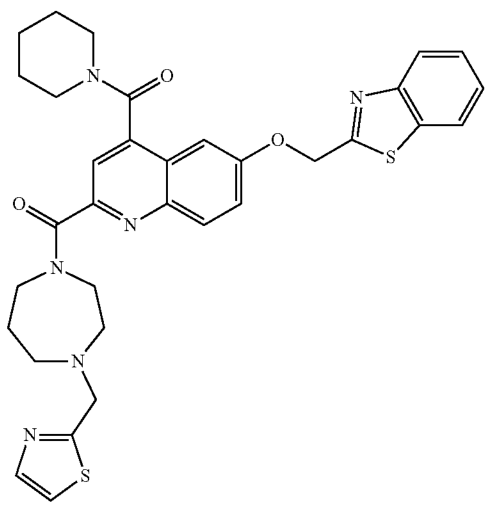 [SMILES: O=C(c1cc(C(=O)N2CCCCC2)c2cc(OCc3nc4ccccc4s3)ccc2n1)N1CCCN(Cc2nccs2)CC1] | 4-(6-(benzo[d]thiazol-2-yl-methoxy)-4-(piperidine-1-carbonyl)quinoline-2-carbonyl)-1-(thiazol-2-yl-methyl)-1,4-diazepan-1-ium 2,2,2-trifluoroacetate | 627.3 |
| 72 | 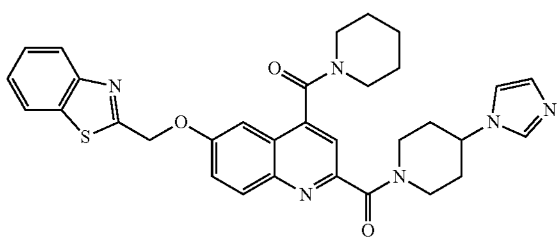 [SMILES: O=C(c1cc(C(=O)N2CCCCC2)c2cc(OCc3nc4ccccc4s3)ccc2n1)N1CCC(n2ccnc2)CC1] | (4-(1H-imidazol-1-yl)-piperidin-1-yl)(6-(benzo-[d]thiazol-2-ylmethoxy)-4-(piperidine-1-carbonyl)-quinolin-2-yl)methanone | 581.2 |
| 73 | 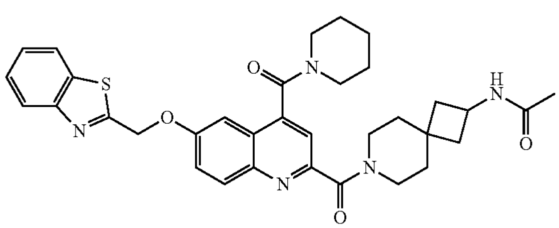 [SMILES: CC(=O)NC1CC2(CCN(C(=O)c3cc(C(=O)N4CCCCC4)c4cc(OCc5nc6ccccc6s5)ccc4n3)CC2)C1] | N-(7-(6-(benzo[d]thiazol-2-ylmethoxy)-4-(piperidine-1-carbonyl)quinoline-2-carbonyl)-7-azaspiro-[3.5]nonan-2-yl)acetamide | 612.2 |
| 74 | 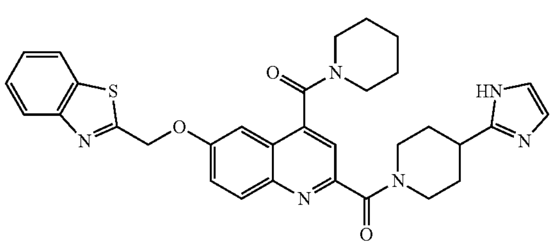 [SMILES: O=C(c1cc(C(=O)N2CCCCC2)c2cc(OCc3nc4ccccc4s3)ccc2n1)N1CCC(c2ncc[nH]2)CC1] | (4-(1H-imidazol-2-yl)-piperidin-1-yl)(6-(benzo-[d]thiazol-2-ylmethoxy)-4-(piperidine-carbonyl)-quinolin-2-yl)methanone | 581.5 |

Example 75

(4-(1H-pyrazol-1-yl)piperidin-1-yl)(6-(benzo[d]thiazol-2-ylmethoxy)-7-fluoro-4-(piperidine-1-carbonyl)quinolin-2-yl)methanone

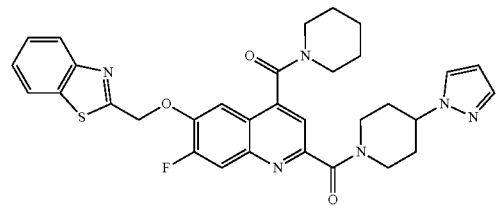

Synthetic Scheme

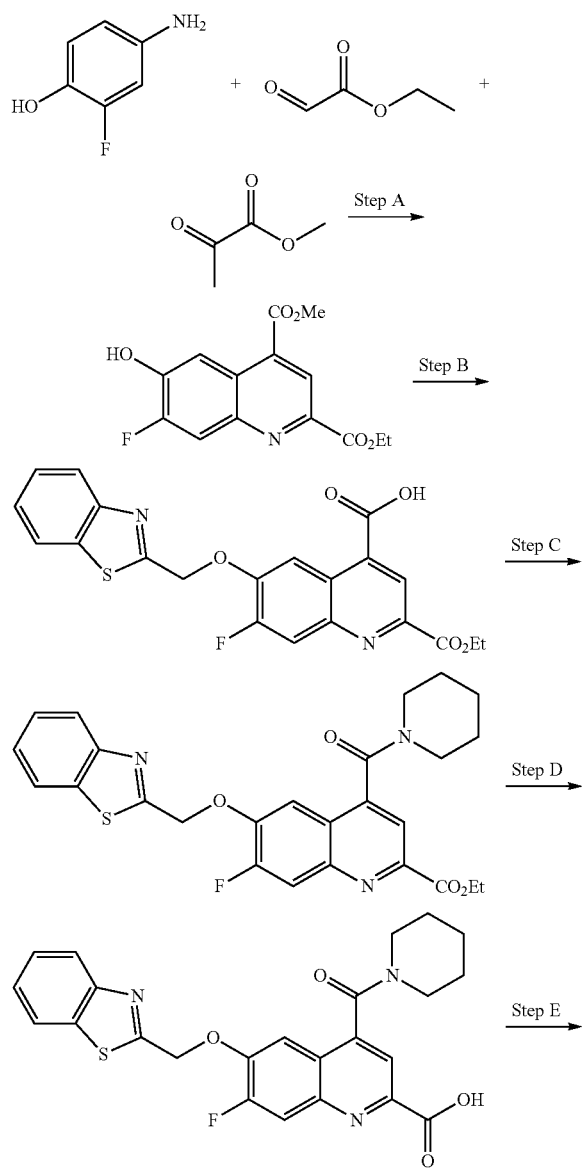

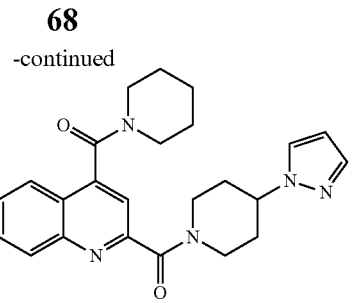

Step A: 2-ethyl 4-methyl 7-fluoro-6-hydroxyquinoline-2,4-dicarboxylate

To a 250 mL round-bottom flask was added a solution of 4-amino-2-fluorophenol (1 g, 7.87 mmol), methyl 2-oxopropanoate (0.964 g, 9.44 mmol), ethyl 2-oxoacetate (0.803 g, 7.87 mmol) in 100 mL of acetonitrile, followed by addition of diiodine (0.100 g, 0.393 mmol). The resulting mixture was stirred at 40° C. for 16 h. The reaction mixture was concentrated in vacuo. The residue was purified by flash column chromatography on silica gel (eluting with 0-20% MeOH in DCM) to give the 2-ethyl 4-methyl 7-fluoro-6-hydroxyquinoline-2,4-dicarboxylate. MS (ESI) m/z 293.97 (M+H)

Step B: 6-(benzo[d]thiazol-2-ylmethoxy)-2-(ethoxycarbonyl)-7-fluoroquinoline-4-carboxylic Acid To a stirred mixture of 2-ethyl 4-methyl 7-fluoro-6-hydroxyquinoline-2,4-dicarboxylate (200 mg, 0.682 mmol) and 2-(bromomethyl)benzo[d]thiazole (156 mg, 0.682 mmol) in DMF (3 ml) was added cesium carbonate (444 mg, 1.364 mmol). The reaction mixture was stirred at rt overnight. The reaction mixture was purified by reverse phase HPCL to provide 6-(benzo[d]thiazol-2-ylmethoxy)-2-(ethoxycarbonyl)-7-fluoroquinoline-4-carboxylic acid. MS (ESI) m/z 426.89 (M+H)

Step C: ethyl 6-(benzo[d]thiazol-2-ylmethoxy)-7-fluoro-4-(piperidine-1-carbonyl)quinoline-2-carboxylate To a stirred mixture of 6-(benzo[d]thiazol-2-ylmethoxy)-2-(ethoxycarbonyl)-7-fluoroquinoline-4-carboxylic acid (30 mg, 0.070 mmol), piperidine (5.99 mg, 0.070 mmol) and N-ethyl-N-isopropylpropan-2-amine (45.5 mg, 0.352 mmol) in DMF (2 ml) was added 2-(3H-[1,2,3]triazolo[4,5-b]pyridin-3-yl)-1,1,3,3-tetramethylisouronium hexafluorophosphate(V) (53.5 mg, 0.141 mmol) at rt under $N_2$. The reaction mixture was stirred for 2 h. The reaction mixture was concentrated and purified by reverse phase HPCL to provide ethyl 6-(benzo[d]thiazol-2-ylmethoxy)-7-fluoro-4-(piperidine-1-carbonyl)quinoline-2-carboxylate. MS (ESI) m z 493.96 (M+H)

Step D: 6-(benzo[d]thiazol-2-ylmethoxy)-7-fluoro-4-(piperidine-1-carbonyl)quinoline-2-carboxylic acid To a stirred mixture of ethyl 6-(benzo[d]thiazol-2-ylmethoxy)-7-fluoro-4-(piperidine-1-carbonyl)quinoline-2-carboxylate (20 mg, 0.041 mmol) in THE (2 ml) was added LiOH (2.91 mg, 0.122 mmol), followed by addition of 0.2 ml of $H_2O$ and 0.2 mL of MeOH. The reaction mixture was stirred at rt overnight. The reaction mixture was filtered through a syringe filter and the filtrate was purified by reverse phase HPLC to give 6-(benzo[d]thiazol-2-yl-methoxy)-7-fluoro-4-(piperidine-1-carbonyl)quinoline-2-carboxylic acid. MS (ESI) m/z 465.92 (M+H)

Step E: (4-(1H-pyrazol-1-yl)piperidin-1-yl)(6-(benzo[d]thiazol-2-ylmethoxy)-7-fluoro-4-(piperidine-1-carbonyl)quinolin-2-yl)methanone To a stirred mixture of 6-(benzo[d]thiazol-2-ylmethoxy)-7-fluoro-4-(piperidine-1-carbonyl)quinoline-2-carboxylic acid (10 mg, 0.021 mmol), 4-(1H-pyrazol-1-yl)piperidine (3.25 mg, 0.021 mmol) and N-ethyl-N-isopropylpropan-2-amine (13.88 mg, 0.107 mmol) in DMF (2 ml) was added 2-(3H-[1,2,3]triazolo[4,5-b]pyridin-3-yl)-1,1,3,3-tetramethylisouronium hexafluorophosphate(V) (16.34 mg, 0.043 mmol) at rt under N$_2$. The reaction mixture was filtered through a syringe filter and the crude was purified by reverse phase HPLC to provide (4-(1H-pyrazol-1-yl)piperidin-1-yl)(6-(benzo[d]thiazol-2-ylmethoxy)-7-fluoro-4-(piperidine-1-carbonyl)quinolin-2-yl)methanone. MS (ESI) m/z 599.29 (M+H)

Example 76

1-(6-(benzo[d][1,2,3]thiadiazol-5-ylmethoxy)-4-(piperidine-1-carbonyl)quinoline-2-carbonyl)-4-(1H-pyrazol-1-yl)piperidine-4-carbonitrile

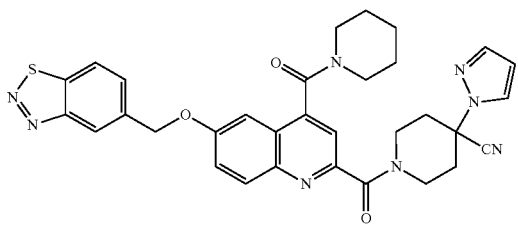 [SMILES: N#CC1(n2cccn2)CCN(C(=O)c2cc(C(=O)N3CCCCC3)c3cc(OCc4ccc5snnc5c4)ccc3n2)CC1]

Synthetic Scheme

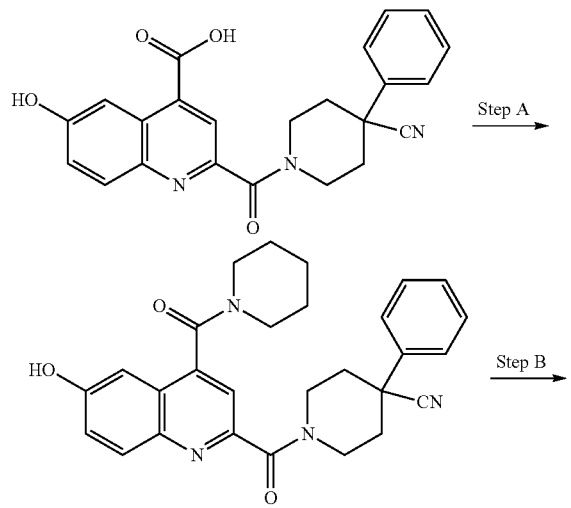

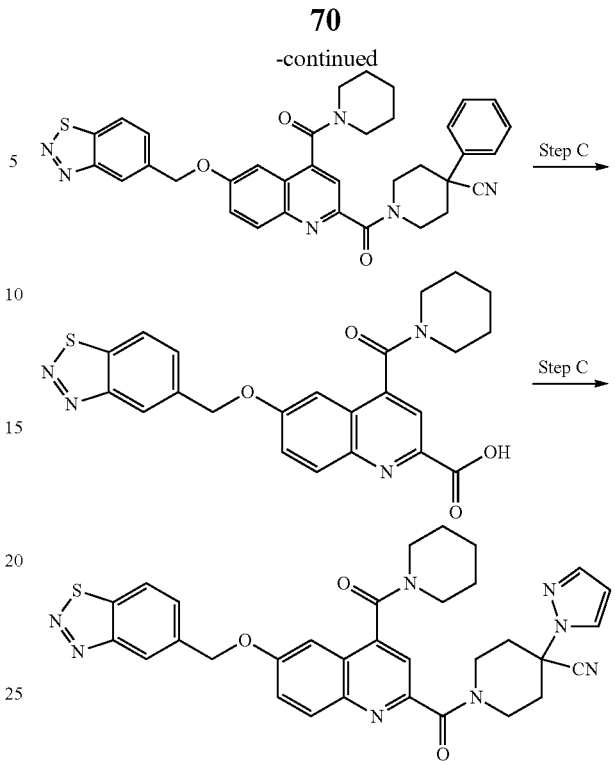

Step A. 1-(6-hydroxy-4-(piperidine-1-carbonyl)quinoline-2-carbonyl)-4-phenylpiperidine-4-carbonitrile To a solution of 2-(4-cyano-4-phenylpiperidine-1-carbonyl)-6-hydroxyquinoline-4-carboxylic acid (527 mg, 1.313 mmol) in DMF (4 ml) was added HATU (549 mg, 1.444 mmol), piperidine (0.156 ml, 1.575 mmol) and DIEA (0.459 ml, 2.63 mmol). The reaction was stirred at room temperature for 3 h. The mixture was concentrated and purified by flash column chromatography on silica gel (eluting with 0-100% (3:1 EtOAC: MeOH) in hexane) to provide 1-(6-hydroxy-4-(piperidine-1-carbonyl)quinoline-2-carbonyl)-4-phenylpiperidine-4-carbonitrile. MS (ESI) m z 469.4 (M+H).

Step B. 1-(6-(benzo[d][1,2,3]thiadiazol-5-ylmethoxy)-4-(piperidine-1-carbonyl)quinoline-2-carbonyl)-4-phenylpiperidine-4-carbonitrile Cs$_2$CO$_3$ (1273 mg, 3.91 mmol) was added to a stirred, cooled 0° C. mixture of 1-(6-hydroxy-4-(piperidine-1-carbonyl)quinoline-2-carbonyl)-4-phenylpiperidine-4-carbonitrile (610 mg, 1.302 mmol) in DMF (4 ml) and the mixture was stirred at 0° C. for 10 min. Then 5-(bromomethyl)-1,2,3-benzothiadiazole (328 mg, 1.432 mmol) was added to the mixture. The reaction was stirred at room temperature overnight. The mixture was purified by flash column chromatography on silica gel (eluting with 0-100% (3:1 EtOAC: MeOH) in hexane to give 1-(6-(benzo[d][1,2,3]thiadiazol-5-ylmethoxy)-4-(piperidine-1-carbonyl)quinoline-2-carbonyl)-4-phenylpiperidine-4-carbonitrile. MS (ESI) m/z 617.4 (M+H).

Step C. 6-(benzo[d][[1,2,3]thiadiazol-5-ylmethoxy)-4-(piperidine-]-carbonyl)quinoline-2-carboxylic Acid To a solution of 1-(6-(benzo[d][1,2,3]thiadiazol-5-ylmethoxy)-4-(piperidine-1-carbonyl)quinoline-2-carbonyl)-

4-phenylpiperidine-4-carbonitrile (746 mg, 1.210 mmol) in THF (4 ml)/Water (1.000 ml)/MeOH (1.000 ml) was added lithium hydroxide (116 mg, 4.84 mmol). The reaction mixture was stirred at 50° C. overnight. The reaction was added to water and acidified with 2M HCl to pH=2. The resulting mixture was filtered, and the filter cake was washed with water to provide 6-(benzo[d][1,2,3]thiadiazol-5-yl-methoxy)-4-(piperidine-1-carbonyl)quinoline-2-carboxylic acid hydrochloride. MS (ESI) m/z 449.3 (M+H).

Step D 1-(6-(benzo[d][[1,2,3]thiadiazol-5-yl-methoxy)-4-(piperidine-]-carbonyl)quinoline-2-carbonyl)-4-(1H-pyrazol-1-yl)piperidine-4-carbonitrile To a solution of 6-(benzo[d][1,2,3]thiadiazol-5-yl-methoxy)-4-(piperidine-1-carbonyl)quinoline-2-carboxylic acid hydrochloride (80 mg, 0.165 mmol) in DMF (1.5 ml) was added HATU (69.0 mg, 0.181 mmol). The mixture was stirred at for 5 min, then 4-(1H-pyrazol-1-yl)piperidine-4-carbonitrile 2,2,2-trifluoroacetate (71.8 mg, 0.247 mmol) and DIEA (0.115 ml, 0.660 mmol) were added to the mixture. The reaction was stirred at room temperature for 18 h. The mixture was purified by reverse phase HPLC. The TFA salt was treated with EtOAc and saturated aq. NaHCO$_3$. The layers were separated and the aq. layer was extracted with EtOAc. The combined organics were dried over MgSO$_4$, filtered and concentrated to provide 1-(6-(benzo[d][1,2,3]thiadiazol-5-ylmethoxy)-4-(piperidine-1-carbonyl)quinoline-2-carbonyl)-4-(1H-pyrazol-1-yl)piperidine-4-carbonitrile. MS (ESI) m/z 607.4 (M+H)

Inhibition of FXIIa Mediated Activation of FXI

Activation of Human Factor XI to XIa by Human Factor α-XIIa

The assay was performed in 50 mM HEPES, 150 mM NaCl, 5 mM CaCl$_2$, 0.1% PEG-8000, pH 7.4 buffer in black, flat-bottom, polystyrene microplates (Corning, Cat #3573). Serial dilutions (10-point, 3.333-fold) of the test compounds delivered as 10 mM DMSO stocks were prepared in the Labcyte Echo-qualified PP 384 well microplates (Labcyte, Cat #P-05525). Human coagulation factor (F)XI (Haematologic Technologies Inc., Cat #HCXI-150, concentration 46 nM, 19.5 uL) was pre-incubated with 0.5 uL of the test compounds for 30 min at 22° C. The activation was initiated by addition of 10 uL of human coagulation factor (F)XIIa (Enzyme Research Laboratories, Cat #HFXIIa, concentration 30 nM) and the reaction proceeded for 60 min at 22° C., after which it was quenched by addition of a selective inhibitor of FXIIa (Compound 54 in International Patent Publication WO2018093695) concentration 600 uM in DMSO, 1 uL). 10 min after the quench, 29 uL of z-GPR-AFC substrate (Sigma, Cat #C0980-10 MG, concentration 200 uM) was added into each well and the detection reaction proceeded for 60 min at 22° C. Fluorescence at 405/510 nm was measured in end-point mode using an Envision plate-reader (Perkin Elmer). IDBS Activity Base XE (ABase) analysis using 4 parameter logistic fit was performed to determine Minimum, Maximum, EC50, and Slope Factor for each compound.

| Example # | Inhibition of FXIIa meditated activation of FXI (nM) |
| --- | --- |
| 1 | 21.76 |
| 2 | 32.23 |
| 3 | 39.57 |
| 4 | 9.595 |
| 5b | 38.83 |
| 5a | 31.77 |
| 6 | 49.18 |
| 7 | 19.47 |
| 8 | 18.77 |
| 9 | 39.65 |
| 10 | 21.76 |
| 11 | 35.07 |
| 12 | 16.79 |
| 13 | 19.97 |
| 14 | 14.68 |
| 15 | 23.71 |
| 16 | 32.93 |
| 17 | 50.83 |
| 18 | 21.86 |
| 19 | 31.61 |
| 20 | 35.76 |
| 21 | 34.34 |
| 22 | 44.61 |
| 23 | 36.61 |
| 24 | 28.91 |
| 25 | 34.25 |
| 26 | 28.86 |
| 27 | 39.03 |
| 28 | 38.86 |
| 29 | 39.69 |
| 30 | 30.06 |
| 31 | 24.89 |
| 32 | 46.88 |
| 33 | 35.92 |
| 34 | 41.37 |
| 35 | 37.7 |
| 36 | 29.14 |
| 37 | 48.18 |
| 38 | 49.48 |
| 39 | 31.83 |
| 40 | 49.92 |
| 41 | 30.48 |
| 42 | 48.73 |
| 43 | 38.54 |
| 44 | 44.57 |
| 45 | 36.92 |
| 46 | 33.69 |
| 47 | 13.78 |
| 48 | 44.94 |
| 49 | 15.03 |
| 50 | 33.14 |
| 51 | 40.5 |
| 52 | 28.31 |
| 53 | 62.57 |
| 54 | 71.54 |
| 55 | 366 |
| 56 | 34.08 |
| 57 | 21.8 |
| 58 | 33.7 |
| 59 | 59.96 |
| 60 | 37.75 |
| 61 | 131 |
| 62 | 19.13 |
| 63 | 31.05 |
| 64 | 42.1 |
| 65 | 19.11 |
| 66 | 16.47 |
| 67 | 34.69 |
| 68 | 19.08 |
| 69 | 45.91 |
| 70 | 40.22 |
| 71 | 48.61 |
| 72 | 112.1 |
| 73 | 38.54 |
| 74 | 32.63 |
| 75 | 18.78 |
| 76 | 10.16 |

What is claimed is:

1. A compound of the formula:

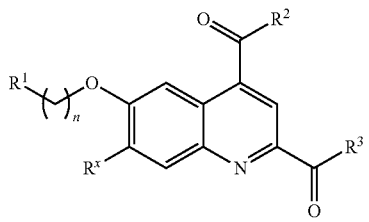

wherein
- $R^1$ is phenyl or heteroaryl, which may be monocyclic or bicyclic, wherein said phenyl and heteroaryl groups are optionally substituted with one to three substituents independently selected from the group consisting of halo, oxo, cyano, $R^4$, $OR^4$, $R^6$ and $NO_2$;
- $R^2$ is piperidinyl, $NR^4R^5$ or $NR^4R^6$, wherein said piperidinyl group is optionally substituted with one to three halo;
- $R^3$ is heterocyclyl, which may be monocyclic or bicyclic, or $NHC(CH_3)_2R^6$, wherein said heterocyclyl is optionally substituted with one to three substituents independently selected from the group consisting of halo, cyano, $R^4$, $OR^4$, $R^6$, $CONR^4R^5$, $NR^4COR^5$, ($C_{1-3}$ alkyl) $R^6$ and $SO_2R^4$,
- $R^4$ is hydrogen or $C_{1-6}$ alkyl, which is optionally substituted with one to three halo;
- $R^5$ is hydrogen or $C_{1-6}$ alkyl, which is optionally substituted with one to three halo;
- $R^6$ is phenyl, $C_{3-6}$ cycloalkyl, heterocyclyl or heteroaryl, wherein said heteroaryl is optionally substituted with one to three substituents independently selected from the group consisting of $C_{1-6}$ alkyl and halo;
- $R^x$ is hydrogen, halo or $C_{1-6}$ alkyl;
- n is an integer from one to three;

or a pharmaceutically acceptable salt thereof.

2. The compound of claim 1 wherein $R^1$ is selected from benzoimidazolyl, benzoisoxazolyl, benzooxadiazolyl, benzooxazolyl, benzothiadiazolyl, benzothiazolyl, benzotriazolyl, dihydroindazolyl, dihydroisobenzofuranyl, imidazopyridinyl, phenyl, pyrazolopyridinyl, pyridinyl or pyrrolyl wherein said groups are optionally substituted with one or two substituents independently selected from the group consisting of methyl, chloro, fluoro, oxo, cyano, $NO_2$, $CF_3$, $OCHF_2$, $OCF_3$ and $OCH_3$; or a pharmaceutically acceptable salt thereof.

3. The compound of claim 1 wherein $R^2$ is piperidinyl, or a pharmaceutically acceptable salt thereof.

4. The compound of claim 1 wherein $R^3$ is piperidinyl, piperazinyl, azaspirooctanyl or pyrrolidinyl, wherein said groups are optionally substituted with one or two substituents independently selected from the group consisting of methyl, fluoro, hydroxyl, cyano, pyrazolyl, phenyl, triazolyl, piperidinyl, $CONH_2$, $NHCOCH_3$, $CH_2CF_3$, $CH(CH_3)CF_3$, $CH_2CHF_2$, and $SO_2CH_3$; or a pharmaceutically acceptable salt thereof.

5. The compound of claim 1 wherein $R^3$ is piperidinyl, which is optionally substituted with one or two substituents independently selected from the group consisting of methyl, fluoro, hydroxyl, cyano, pyrazolyl, phenyl, triazolyl, piperidinyl, $CONH_2$, $NHCOCH_3$, $CH_2CF_3$, $CH(CH_3)CF_3$, $CH_2CHF_2$, and $SO_2CH_3$; or a pharmaceutically acceptable salt thereof.

6. The compound of claim 1 wherein $R^1$ is heteroaryl, which is bicyclic, and is optionally substituted with one to three substituents independently selected from the group consisting of halo, oxo, cyano and $R^4$; or a pharmaceutically acceptable salt thereof.

7. A compound selected from

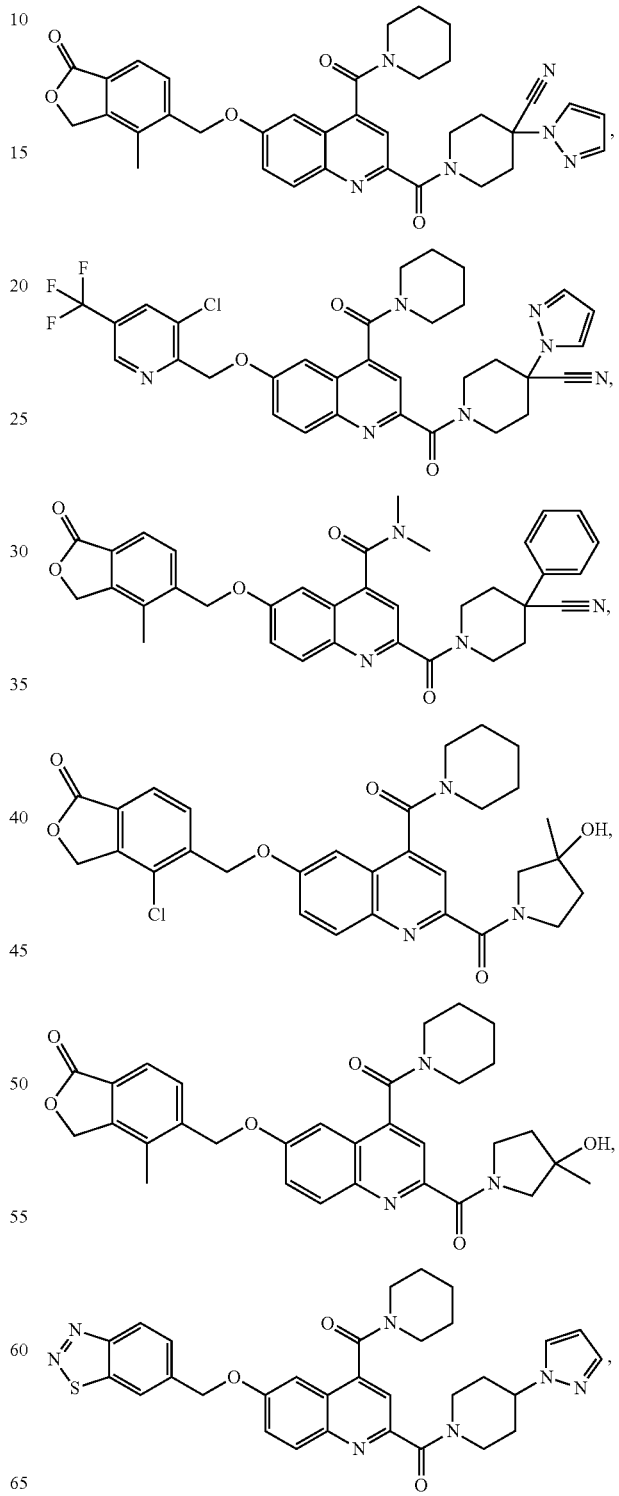

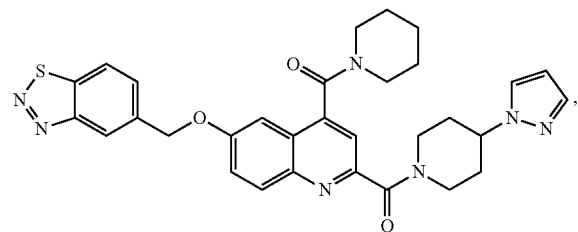
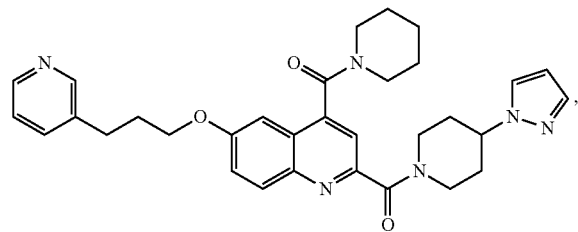
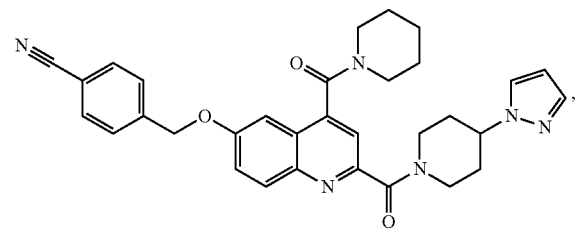
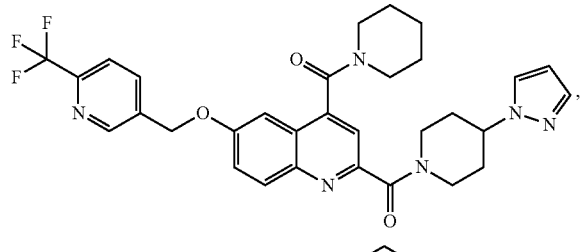
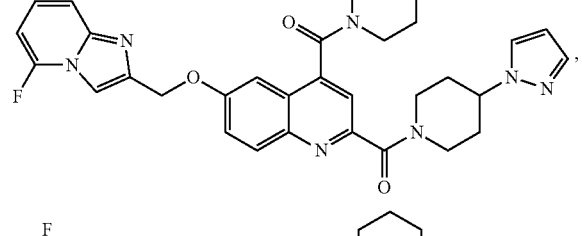
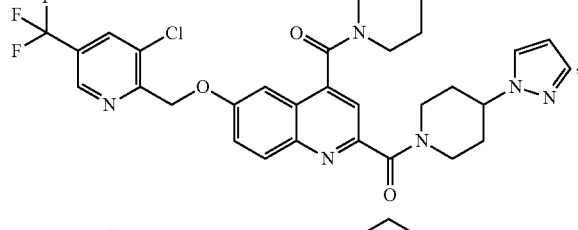
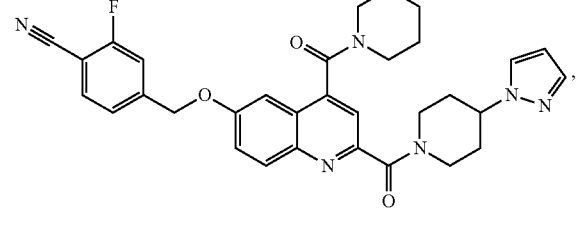
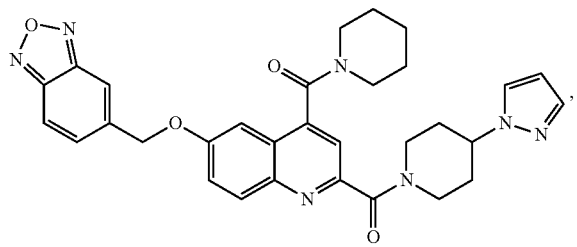
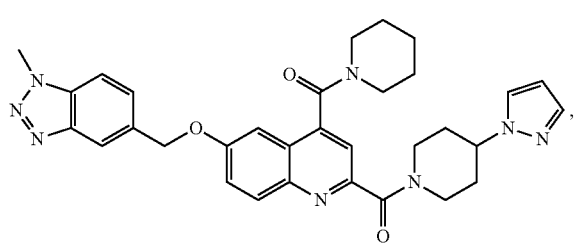
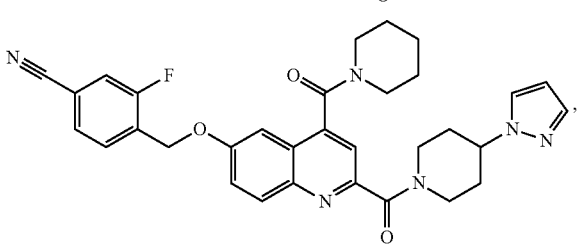
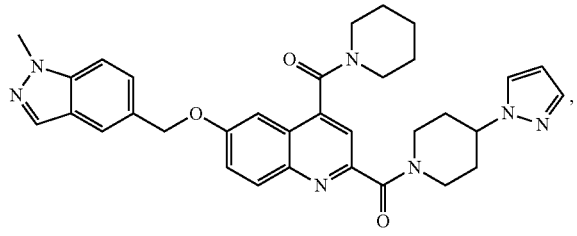
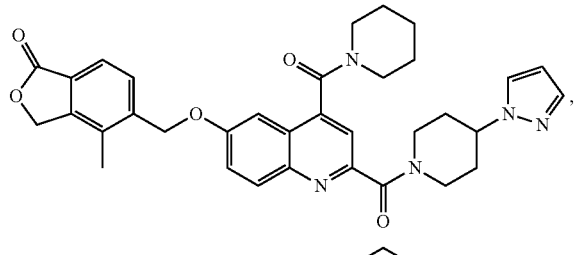
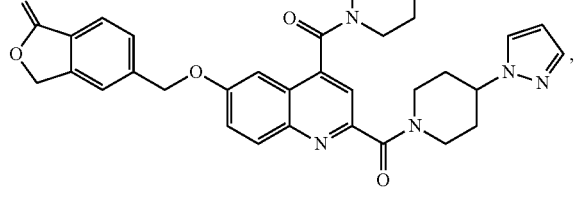
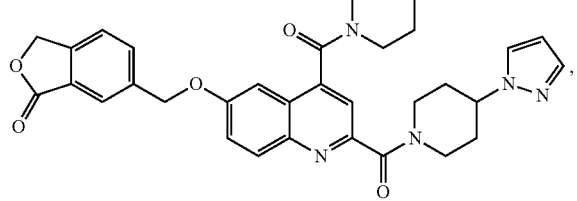

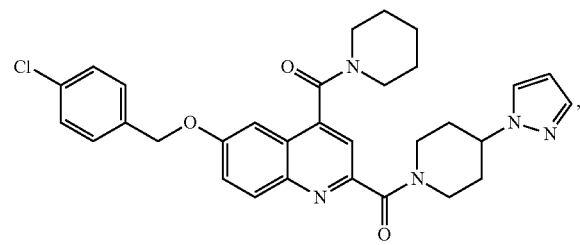,
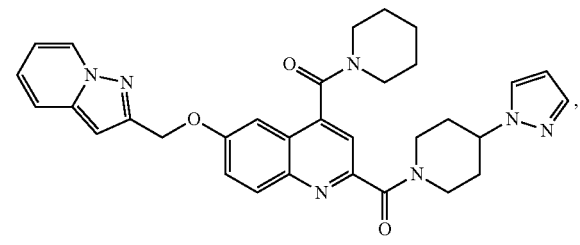,
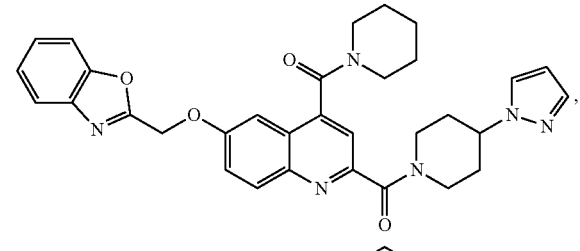,
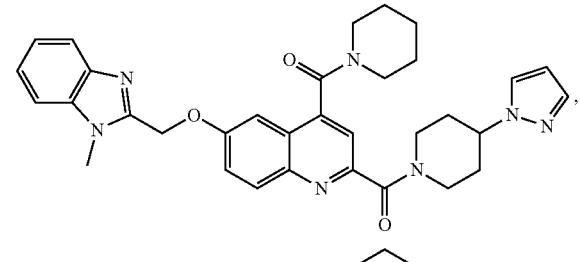,
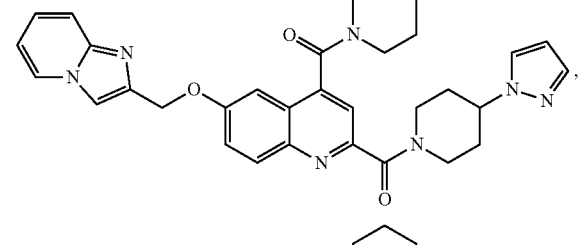,
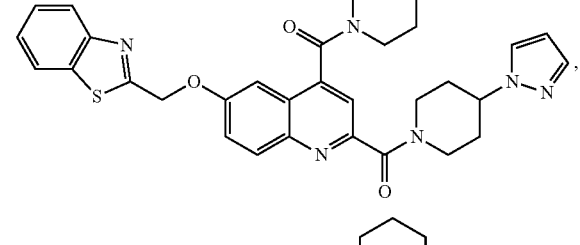,
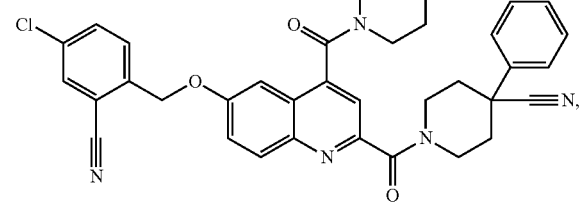,
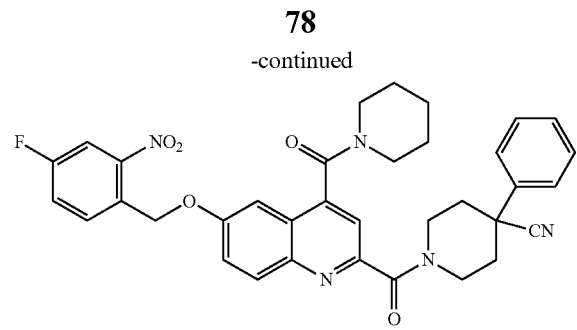,
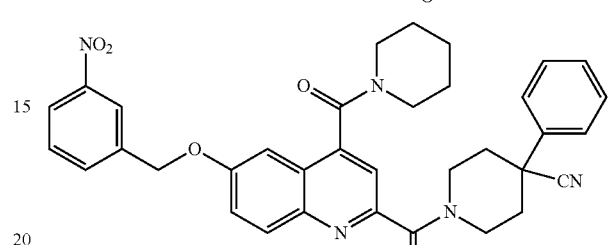,
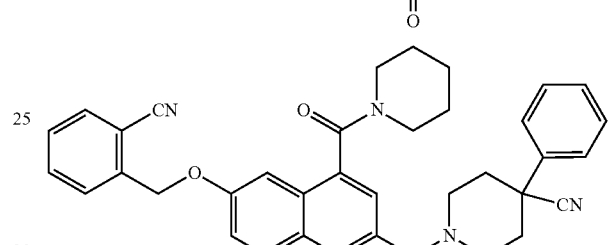,
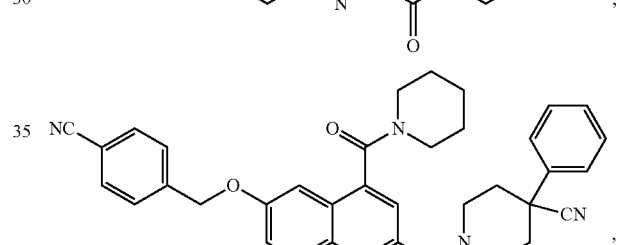,
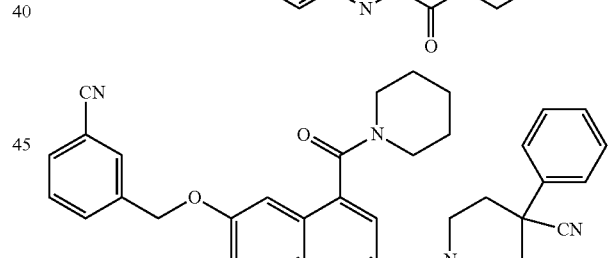,
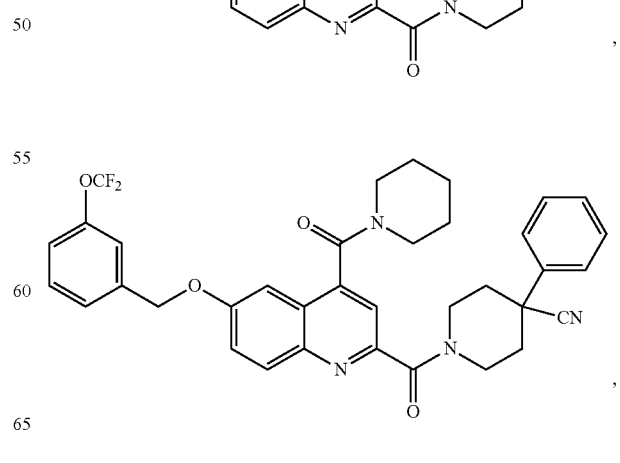, -continued
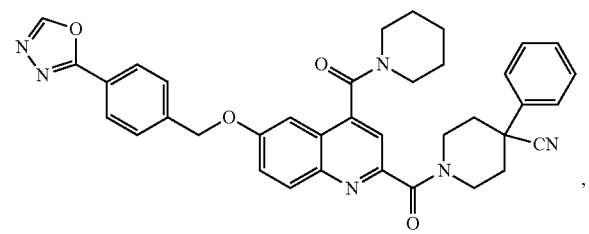
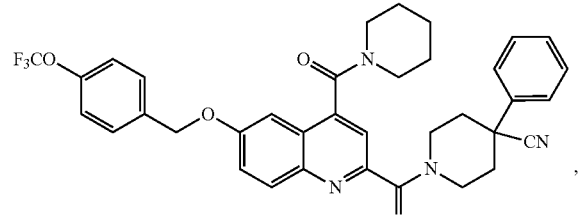
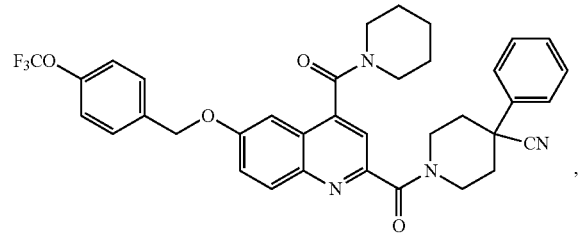
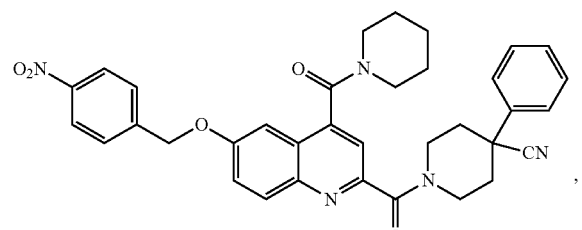
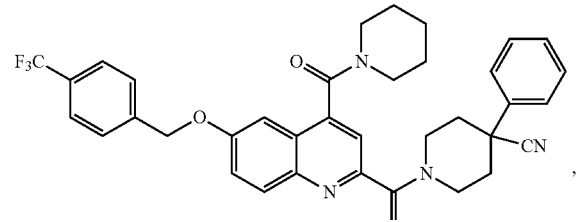
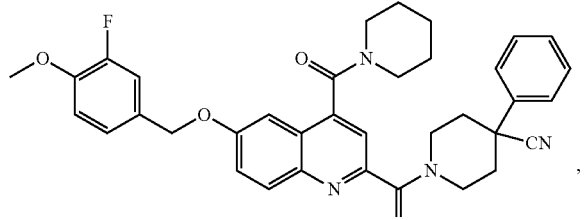
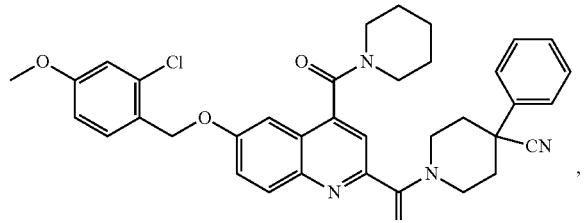
-continued
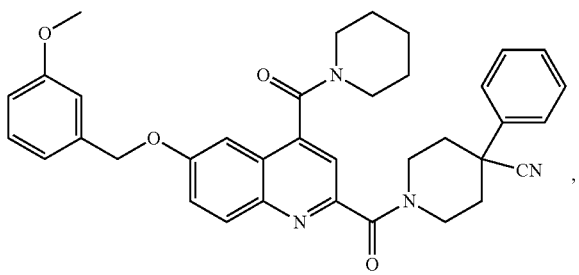
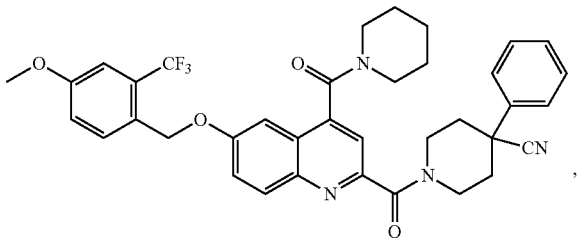
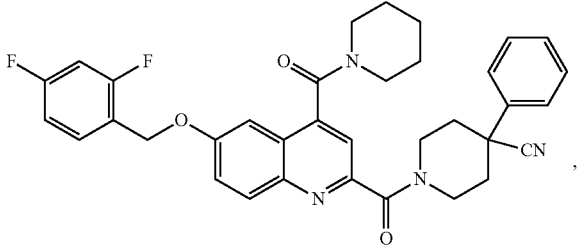
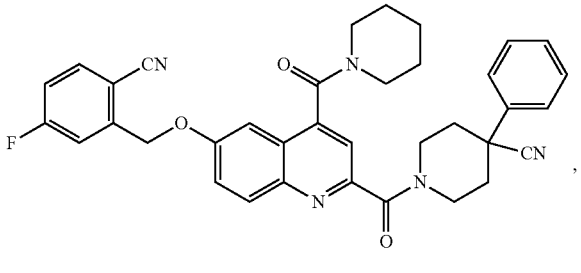
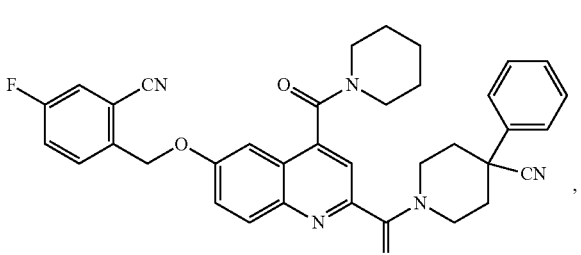
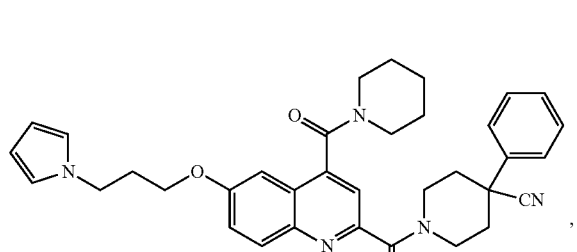

-continued
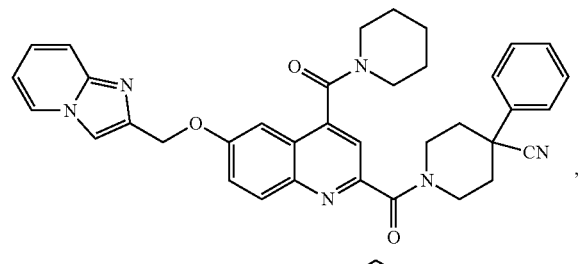
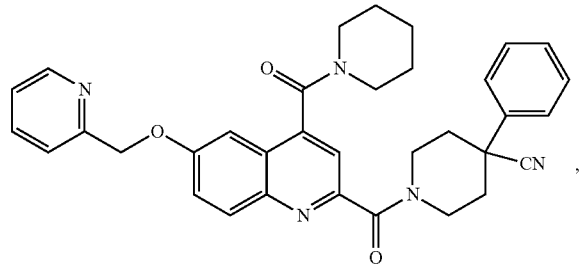
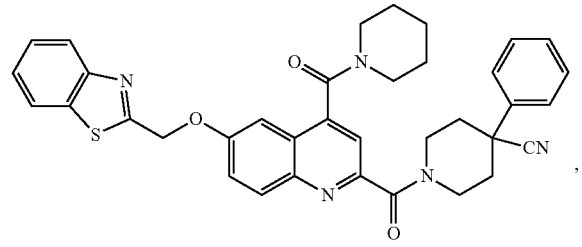
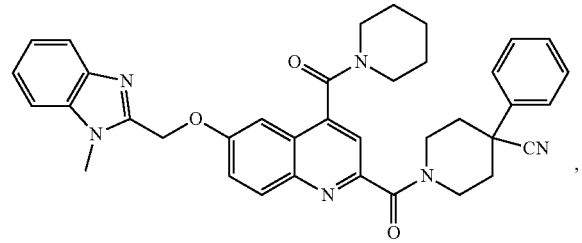
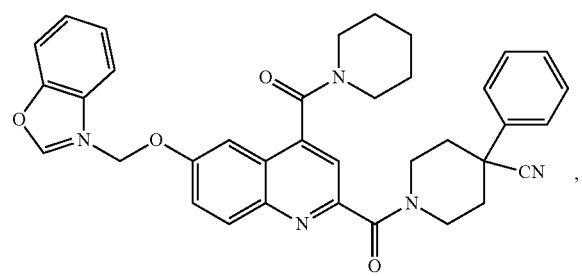
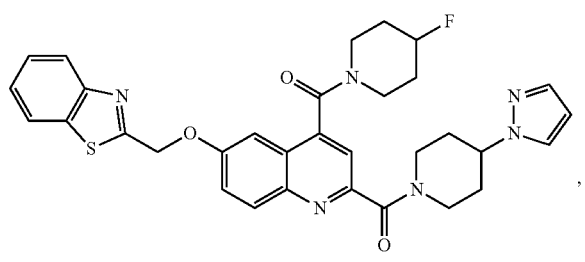
-continued
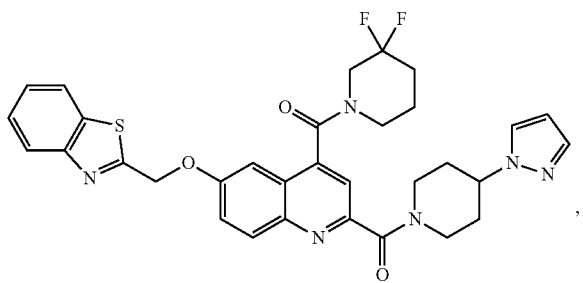
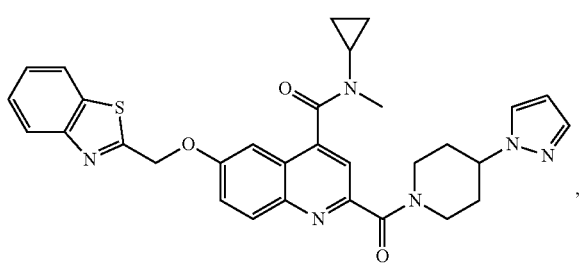
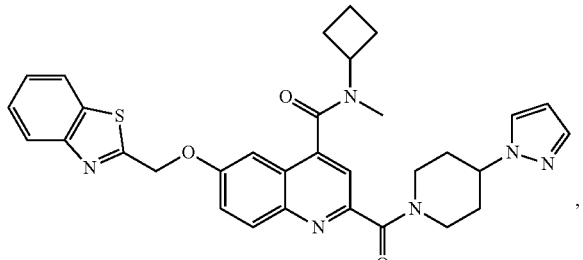
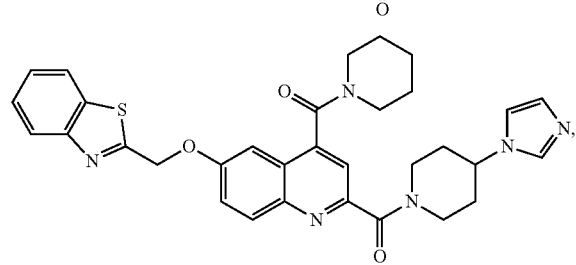
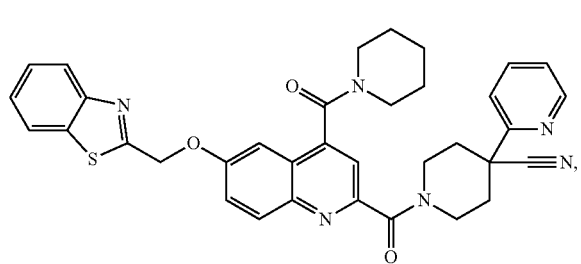
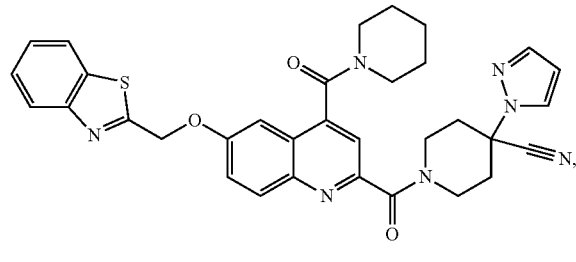

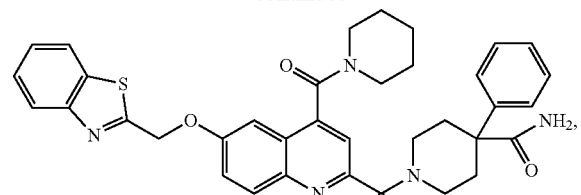
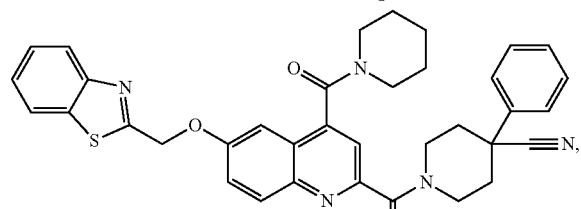
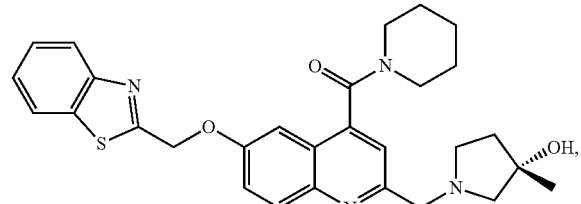
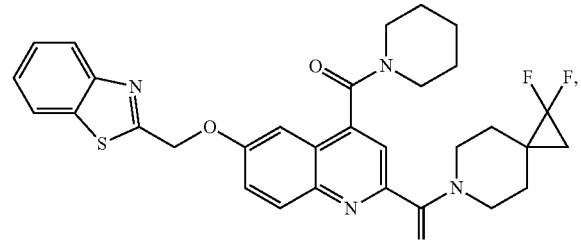
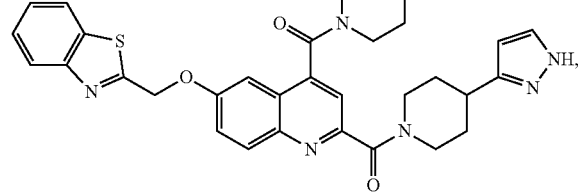
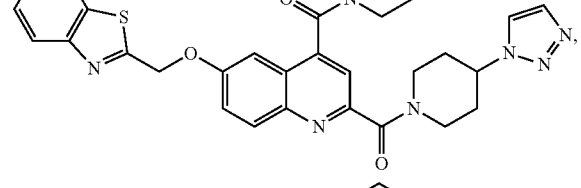
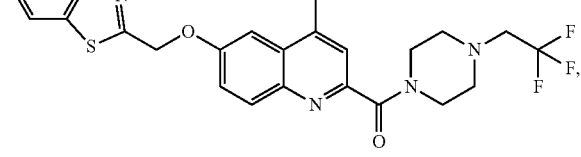
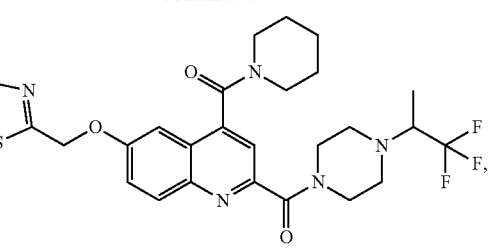
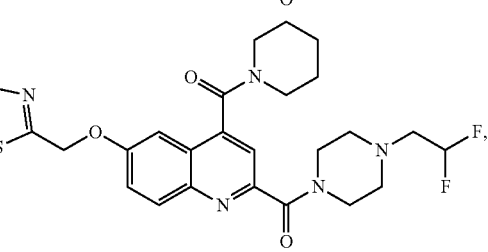
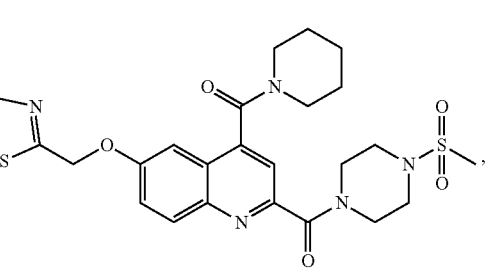
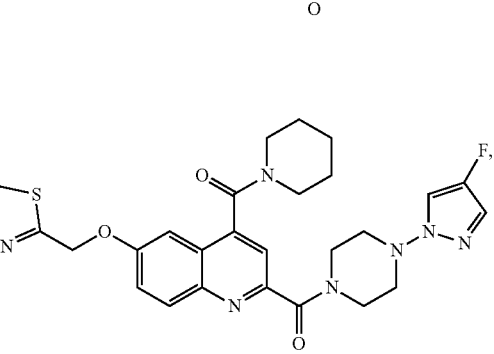
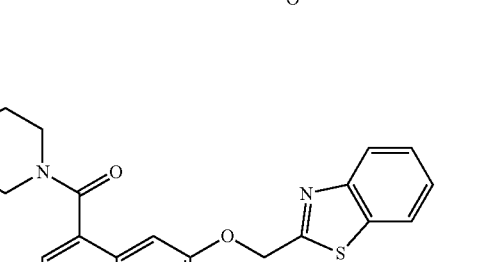
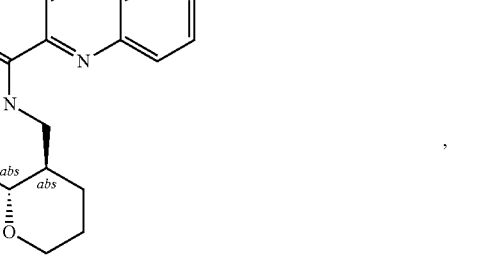

-continued

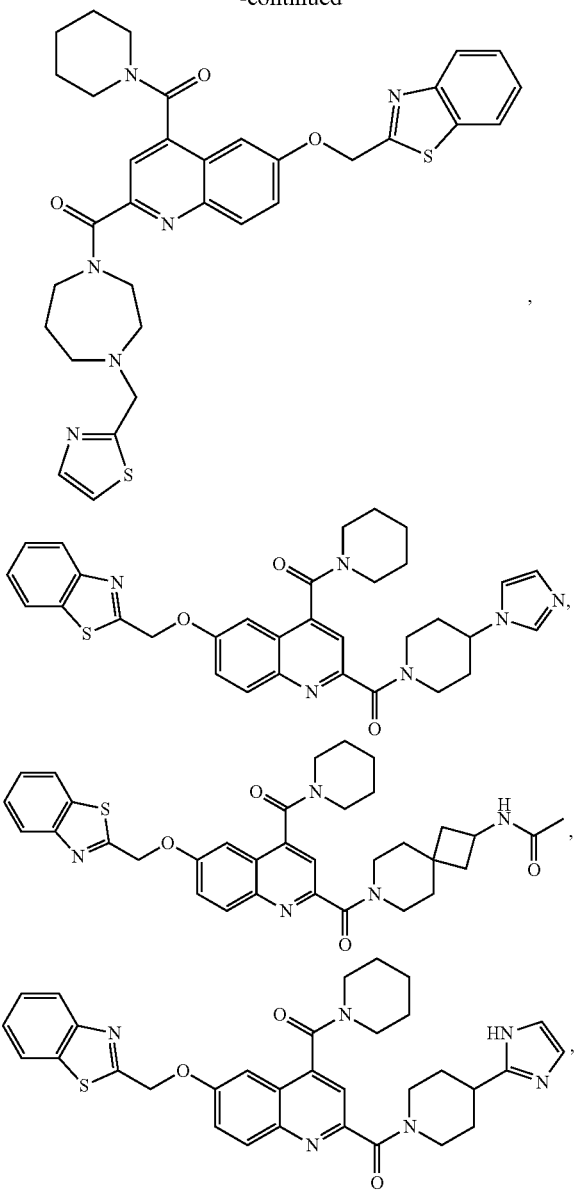

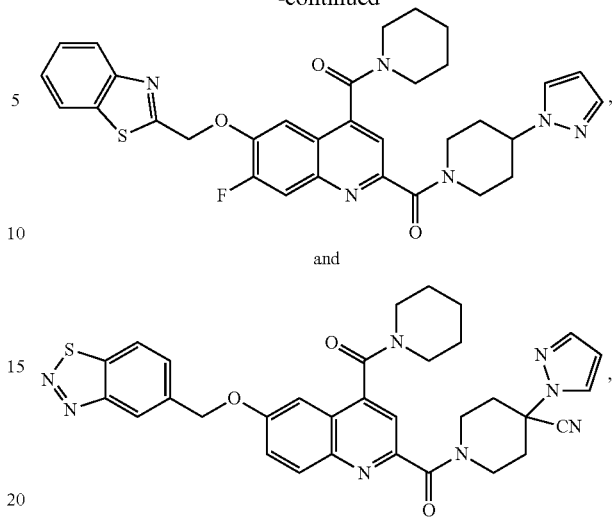

or a pharmaceutically acceptable salt thereof.

8. A pharmaceutical composition comprising a compound of claim 1 or a pharmaceutically acceptable salt thereof and a pharmaceutically acceptable carrier.

9. A method for inhibiting thrombus formation in blood or treating thrombus formation in blood comprising administering a pharmaceutical composition of claim 8 to a mammal in need of thereof.

10. A method for preventing thrombus formation in blood comprising administering a pharmaceutical composition of claim 8 to a mammal in need thereof.

11. A method of treating venous thromboembolism or pulmonary embolism in a mammal comprising administering a pharmaceutical composition of claim 8 to a mammal in need thereof.

12. A method of treating deep vein thrombosis in a mammal comprising administering a pharmaceutical composition of claim 8 to a mammal in need thereof.

13. A method of treating thromboembolic stroke in a mammal comprising administering a pharmaceutical composition of claim 8 to a mammal in need thereof.

* * * * *